(12) United States Patent
Turner et al.

(10) Patent No.: US 9,856,234 B2
(45) Date of Patent: *Jan. 2, 2018

(54) HETEROCYCLIC COMPOUNDS AND THEIR USE AS GLYCOGEN SYNTHASE KINASE 3 INHIBITORS

(71) Applicants: ABBVIE INC., North Chicago, IL (US); ABBVIE DEUTSCHLAND GMBH & CO. KG, Wiesbaden (DE)

(72) Inventors: Sean Colm Turner, Mannheim (DE); Margaretha Henrica Maria Bakker, Seeheim-Jugenheim (DE); Kent D. Stewart, Gurnee, IL (US)

(73) Assignees: ABBVIE DEUTSCHLAND GMBH & CO. KG, Wiesbaden (DE); ABBVIE INC., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/169,584

(22) Filed: Jan. 31, 2014

(65) Prior Publication Data

US 2014/0148458 A1    May 29, 2014

Related U.S. Application Data

(62) Division of application No. 12/446,233, filed as application No. PCT/EP2007/061231 on Oct. 19, 2007, now Pat. No. 8,642,598.

(60) Provisional application No. 60/936,837, filed on Jun. 22, 2007.

(30) Foreign Application Priority Data

Oct. 21, 2006    (EP) .................................... 06022094

(51) Int. Cl.
| | | |
|---|---|---|
| *C07D 345/00* | (2006.01) | |
| *C07D 517/00* | (2006.01) | |
| *C07D 401/12* | (2006.01) | |
| *C07D 413/14* | (2006.01) | |
| *C07D 471/04* | (2006.01) | |
| *C07D 241/20* | (2006.01) | |

(52) U.S. Cl.
CPC ......... *C07D 401/12* (2013.01); *C07D 241/20* (2013.01); *C07D 413/14* (2013.01); *C07D 471/04* (2013.01)

(58) Field of Classification Search
USPC .......................................................... 540/1
See application file for complete search history.

(56) References Cited

U.S. PATENT DOCUMENTS

| | | | |
|---|---|---|---|
| 7,037,918 B2 | 5/2006 | Nuss et al. | |
| 7,205,314 B2 | 4/2007 | Berg et al. | |
| 8,158,661 B2 | 4/2012 | Medina Padilla et al. | |
| 8,207,216 B2 | 6/2012 | Kozikowski et al. | |
| 8,236,858 B2 | 8/2012 | Peleg-Shulman et al. | |
| 8,318,793 B2 | 11/2012 | Turner et al. | |
| 8,426,425 B2 | 4/2013 | Jimenez et al. | |
| 8,592,437 B2* | 11/2013 | Lochead ............... | C07D 239/36 514/269 |
| 8,686,042 B2 | 4/2014 | Gil et al. | |
| 9,090,592 B2* | 7/2015 | Turner ................. | C07D 401/12 |
| 2002/0177556 A1 | 11/2002 | Engel et al. | |
| 2003/0199526 A1 | 10/2003 | Choquette et al. | |
| 2004/0186288 A1 | 9/2004 | Kruger et al. | |
| 2006/0009460 A1 | 1/2006 | Dickson, Jr. et al. | |

FOREIGN PATENT DOCUMENTS

| | | |
|---|---|---|
| EP | 1256578 A1 | 11/2002 |
| WO | 9921835 A1 | 5/1999 |
| WO | 0112188 A1 | 2/2001 |
| WO | 0210141 A1 | 2/2002 |

(Continued)

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*

(Continued)

*Primary Examiner* — Marcos Sznaidman

(74) *Attorney, Agent, or Firm* — Neal, Gerber & Eisenberg LLP

(57) ABSTRACT

The present invention relates to a heterocyclic compound of the general formula (I) and their use and preparation, methods of making the compounds, compositions containing at least one of said compounds, and methods of treatment using at least one compound. In particular, compounds of the general formula (I) are useful for inhibiting glycogen synthase kinase 3 (GSK-3).

13 Claims, No Drawings

(56) References Cited

FOREIGN PATENT DOCUMENTS

| WO | 0218346 A1 | 3/2002 |
|---|---|---|
| WO | 0222601 A1 | 3/2002 |
| WO | 03004472 A1 | 1/2003 |
| WO | 03035065 A1 | 5/2003 |
| WO | WO-03049739 A1 | 6/2003 |
| WO | WO-03053330 A2 | 7/2003 |
| WO | WO-03053444 A1 | 7/2003 |
| WO | WO-03055492 A1 | 7/2003 |
| WO | WO-03055877 A1 | 7/2003 |
| WO | WO-03082853 A1 | 10/2003 |
| WO | 2004072029 A2 | 8/2004 |
| WO | 2005012256 A1 | 2/2005 |
| WO | 2005019190 A2 | 3/2005 |
| WO | 2005061516 A1 | 7/2005 |
| WO | WO-2005061519 A1 | 7/2005 |
| WO | 2005120509 A1 | 12/2005 |
| WO | WO-2005123672 A2 | 12/2005 |
| WO | 2006003440 A1 | 1/2006 |
| WO | 2006091737 A1 | 8/2006 |
| WO | 2007003525 A2 | 1/2007 |
| WO | 2007017145 A2 | 2/2007 |
| WO | 2007040438 A2 | 4/2007 |
| WO | 2007083978 A1 | 7/2007 |
| WO | WO-2007089192 A1 | 8/2007 |
| WO | WO-2007120102 A1 | 10/2007 |
| WO | 2007125110 A1 | 11/2007 |
| WO | 2008046919 A2 | 4/2008 |
| WO | WO-2008130312 A1 | 10/2008 |
| WO | 2009130317 A1 | 10/2009 |

OTHER PUBLICATIONS

McCubrey JA, Steelman LS, Bertrand FE, Davis NM, Sokolosky M, Abrams SL, Montalto G, D'Assoro AB, Libra M, Nicoletti F, Maestro R, Basecke J, Rakus D, Gizak A, Demidenko ZN, Cocco L, Martelli AM, Cervello M. GSK-3 as potential target for therapeutic intervention in cancer. Oncotarget. May 30, 2014;5(10):2881-911.*
Intelihealth, "Alzheimer's disease," online, accessed Jun. 30, 2008, http://www.intelihealth.com/IH/intlh/WSIHW000/8303/9117/195703.html?d=dmtHealthAZ.*
Intelihealth, "Dementia," online, accessed Sep. 22, 2009, http://www.intelihealth.com/IH/ihtlH/WSIHW000/24479/11184.html.*
Intelihealth, "Obesity" online, accessed Oct. 4, 2011, http://www.intelihealth.com/IH/ihtlH?t=23671&p=~br,IHW|~st,8271|~r,WSIHW000|~b,*|.*
Intelihealth, "Parkinson's disease," online, accessed Sep. 22, 2009, http://www.intelihealth.com/IH/ihtlH?d=dmtHealthAZ&c=201957.*
Intelihealth, "Schizophrenia" online, accessed Oct. 4, 2011, http://www.intelihealth.com/IH/ihtlH/WSIHW000/8271/8694/188010.html?d=dmtHealthAZ#prevent.*
Anderson M.O., et al., "Parallel Synthesis of Diarylureas and their Evaluation as Inhibitors of Insulin-like Growth Factor Receptor," Journal of Combinatorial Chemistry, 2006, vol. 8 (5), pp. 784-790.
Barth et al., "Pyridaiino[3,4-b][1,5]benzoxazepin-5(6H)-ones: synthesis and biological evaluation, CODEN: ACCHEH; ISSN: 0956-3202, XP009074718," Antiviral Chemistry and Chemotherapy, vol. 7 (6), pp. 300-312, 1996.
Heinisch et al., "Pyridazines. 81. A novel 1,2-diazine containing tricyclic system: synthesis of pyridazinol[3,4-b][1,5]benzodiazepin-5-ones as potential HIV-1 reverse transcriptase inhibitors, CODEN: HTCYAM; ISSN: 0385-5414, 1997, XP00124802," HETEROCYC.
Heinisch G., et al., "Synthesis of Pyridazino[3,4-b][1,5]Benzodiazepin-5-ones and their Biological Evaluation as Non-Nucleoside HIV Reverse Transcriptase Inhibitors," Archives of Pharmacology, 1997, vol. 330, pp. 29-34.

Heinisch G., et al., "Synthesis of Substituted Tri- and Tetracyclic Compounds Bearing a Pyridazine Core and their Biological Evaluation as Antimycobacterial Agents," Archives of Pharmacology, 2000, vol. 333, pp. 231-240.
Honma T., et al., "Structure-Based Generation of a New Class of Potent Cdk4 Inhibitors: New de Novo Design Strategy and Library Design," Journal of Medicinal Chemistry, 2001, vol. 44, pp. 4615-4627.
King F.D., Ed., "Bioisosteres, Conformational Restriction and Pro-Drugs-Case History: An Example of a Conformational Restriction Approach," Medical Chemistry: Principles and Practice, 1994, Chapter 14, pp. 206-209.
Ott, Ingo et al., "Substituted Pyridazino[3,4-b][1,5]benzoxazepin-5(6H)on es as Multidrug-Resistance Modulating Agents," Journal of Medicinal Chemistry, vol. 47 (18), pp. 4627-4630, 2004.
Shaw J.T., et al., "The Preparation of 2,6-Diaminopyrazine,2,6-Diazidopyrazine and Some of their Derivatives," Journal of Heterocyclic Chemistry, 1980, vol. 17 (1), pp. 11-16.
Waterbeemd Van De H., et al., "Property-based Design: Optimization of Drug Absorption and Pharmacokinetics," Journal of Medicinal Chemistry, 2001, vol. 44 (9), pp. 1313-1333.
Aho L., et al., "Systematic Appraisal using Immunohistochemistry of Brain Pathology in Aged and Demented Subjects.," Dementia and Geriatric Cognitive Disorders, 2008, vol. 25 (5), pp. 423-432.
Cole A.R., et al., "GSK-3 Phosphorylation of the Alzheimer Epitope Within Collapsin Response Mediator Proteins Regulates Axon Elongation in Primary Neurons.," The Journal of Biological Chemistry, 2004, vol. 279 (48), pp. 50176-50180.
Cotter D., et al., "Abnormalities of Wnt Signalling in Schizophrenia—Evidence For Neurodevelopmental Abnormality," NeuroReport, 1998, vol. 9 (7), pp. 1261-1265.
Cowper-Smith C.D., et al., "Delayed Administration of a Potent Cyclin Dependent Kinase and Glycogen Synthase Kinase 3 Beta Inhibitor Produces Long-Term Neuroprotection in a Hypoxia-Ischemia Model of Brain Injury.," Neuroscience, 2008, vol. 155 (3), pp. 864-875.
De Sarno P., et al., "Lithium Prevents and Ameliorates Experimental Autoimmune Encephalomyelitis.," Journal of Immunology (Baltimore, Md. : 1950), 2008, vol. 181 (1), pp. 338-345.
Elchebly M., et al., "Increased Insulin Sensitivity and Obesity Resistance in Mice Lacking the Protein Tyrosine Phosphatase-1B Gene," Science, 1999, vol. 283 (5407), pp. 1544-1548.
Engel T., et al., "Chronic Lithium Administration to Ftdp-17 Tau and GSK-3Beta Overexpressing Mice Prevents Tau Hyperphosphorylation and Neurofibrillary Tangle Formation, But Pre-Formed Neurofibrillary Tangles Do Not Revert.," Journal of Neurochemistry, 2006, vol. 99 (6), pp. 1445-1455.
Engel T., et al., "Full Reversal of Alzheimer'S Disease-Like Phenotype in a Mouse Model with Conditional Overexpression of Glycogen Synthase Kinase-3.," The Journal of Neuroscience : the Official Journal of the Society For Neuroscience, 2006, vol. 26 (19), pp. 5083-5090.
Gould T.D., et al., "Ar-A014418, a Selective GSK-3 Inhibitor, Produces Antidepressant-Like Effects in the Forced Swim Test.," The International Journal of Neuropsychopharmacology, 2004, vol. 7 (4), pp. 387-390.
Hanger D.P., et al., "Glycogen Synthase Kinase-3 Induces Alzheimer'S Disease-Like Phosphorylation of Tau: Generation of Paired Helical Filament Epitopes and Neuronal Localisation of the Kinase.," Neuroscience Letters, 1992, vol. 147 (1), pp. 58-62.
Imazu M., et al., "Phosphorylation and Inactivation of Liver Glycogen Synthase by Liver Protein Kinases," The Journal of Biological Chemistry, 1984, vol. 259 (3), pp. 1813-1821.
Ishiguro K., et al., "Glycogen Synthase Kinase 3 Beta Is Identical to Tau Protein Kinase I Generating Several Epitopes of Paired Helical Filaments.," Febs Letters, 1993, vol. 325 (3), pp. 167-172.
Kaytor M.D., et al., "The GSK3Beta Signaling Cascade and Neurodegenerative Disease," Current Opinion in Neurobiology, 2002, vol. 12 (3), pp. 275-278.
Koh S-H., et al., "Inhibition of Glycogen Synthase Kinase-3 Suppresses the Onset of Symptoms and Disease Progression of G93A-Sod1 Mouse Model of Als," Experimental Neurology, 2007, vol. 205 (2), pp. 336-346.

(56) References Cited

OTHER PUBLICATIONS

Koros E., et al., "The Role of Glycogen Synthase Kinase-3Beta in Schizophrenia.," Drug News &Amp; Perspectives, 2007, vol. 20 (7), pp. 437-445.
Kypta R.M., et al., "GSK-3 Inhibitors and Their Potential in the Treatment of Alzheimer'S Disease," Expert Opinion On Therapeutic Patents, 2005, vol. 15 (10), pp. 1315-1331.
Leroy K., et al., "Increased Level of Active GSK-3Beta in Alzheimer'S Disease and Accumulation in Argyrophilic Grains and in Neurones at Different Stages of Neurofibrillary Degeneration.," Neuropathology and Applied Neurobiology, 2007, vol. 33 (1), pp. 43-55.
Lijam N., et al., "Social Interaction and Sensorimotor Gating Abnormalities in Mice Lacking Dvl1," Cell, 1997, vol. 90 (5), pp. 895-905.
Lucas J.J., et al., "Decreased Nuclear Beta-Catenin, Tau Hyperphosphorylation and Neurodegeneration in GSK-3Beta Conditional Transgenic Mice.," The Embo Journal, 2001, vol. 20 (1-2), pp. 27-39.
Luna-Muâ±oz J., et al., "Earliest Stages of Tau Conformational Changes Are Related to the Appearance of a Sequence of Specific Phospho-Dependent Tau Epitopes in Alzheimer'S Disease.," Journal of Alzheimer'S Disease : Jad, 2007, vol. 12 (4), pp. 365-375.
Mandelkow E.M., et al., "Glycogen Synthase Kinase-3 and the Alzheimer-Like State of Microtubule-Associated Protein Tau.," Febs Letters, 1992, vol. 314 (3), pp. 315-321.
Martin M., et al., "Toll-Like Receptor-Mediated Cytokine Production Is Differentially Regulated By Glycogen Synthase Kinase 3.," Nature Immunology, 2005, vol. 6 (8), pp. 777-784.
Martins D.F., et al., "The Antinociceptive Effects of Ar-A014418, a Selective Inhibitor of Glycogen Synthase Kinase-3 Beta, in Mice.," The Journal of Pain : Official Journal of the American Pain Society, 2011, vol. 12 (3), pp. 315-322.
Medina., et al., "Medina et al., Frontiers in Molecular Neuroscience, 2011, vol. 4 (24), pp. 1-10.," Frontiers In Molecular Neuroscience, 2011, vol. 4 (24), pp. 1-10.
Noble W., et al., "Inhibition of Glycogen Synthase Kinase-3 By Lithium Correlates with Reduced Tauopathy and Degeneration in Vivo.," Proceedings of the National Academy of Sciences of the United States of America, 2005, vol. 102 (19), pp. 6990-6995.
Onishi T., et al., "A Novel Glycogen Synthase Kinase-3 Inhibitor 2-Methyl-5-(3-{4-[(S)-Methylsulfinyl]Phenyl}-1-Benzofuran-5-Yl)-1,3,4-Oxadiazole Decreases Tau Phosphorylation and Ameliorates Cognitive Deficits in a Transgenic Model of Alzheimer'S Disease.," Journal of Neurochemistry, 2011, vol. 119 (6), pp. 1330-1340.
Pei J.J., et al., "Distribution, Levels, and Activity of Glycogen Synthase Kinase-3 in the Alzheimer Disease Brain.," Journal of Neuropathology and Experimental Neurology, 1997, vol. 56 (1), pp. 70-78.
Peineau S., et al., "Ltp Inhibits Ltd in the Hippocampus Via Regulation of GSK3Beta.," Neuron, 2007, vol. 53 (5), pp. 703-717.
Rockenstein E., et al., "Neuroprotective Effects of Regulators of the Glycogen Synthase Kinase-3Beta Signaling Pathway in a Transgenic Model of Alzheimer'S Disease Are Associated with Reduced Amyloid Precursor Protein Phosphorylation," The Journal of Neuroscience, 2007, vol. 27 (8), pp. 1981-1991.
Rubinfeld B., et al., "Binding of GSK3Beta to the Apc-Beta-Catenin Complex and Regulation of Complex Assembly.," Science (New York, N.Y.), 1996, vol. 272 (5264), pp. 1023-1026.
Soos T.J., et al., "Cdk/GSK-3 Inhibitors as a New Approach for the Treatment of Proliferative Renal Diseases.," Drug News &Amp; Perspectives, 2006, vol. 19 (6), pp. 325-328.
Spillantini M.G., et al., "Tau Protein Pathology in Neurodegenerative Diseases," Trends In Neurosciences, 1998, vol. 21 (10), pp. 428-433.
Szczepankiewicz A., et al., "Association Analysis of the GSK-3Beta T-50C Gene Polymorphism with Schizophrenia and Bipolar Disorder.," Neuropsychobiology, 2006, vol. 53 (1), pp. 51-56.
Takada Y., et al., "Genetic Deletion of Glycogen Synthase Kinase-3Beta Abrogates Activation of Ikappabalpha Kinase, Jnk, Akt, and P44/P42 Mapk But Potentiates Apoptosis Induced By Tumor Necrosis Factor.," The Journal of Biological Chemistry, 2004, vol. 279 (38), pp. 39541-39554.
Whittle B.J., et al., "Reduction of Experimental Colitis in the Rat By Inhibitors of Glycogen Synthase Kinase-3Beta.," British Journal of Pharmacology, 2006, vol. 147 (5), pp. 575-582.
Zhang J., et al., "Tau Protein Is Hyperphosphorylated in a Site-Specific Manner in Apoptotic Neuronal Pc12 Cells.," Journal of Neurochemistry, 2000, vol. 75 (6), pp. 2346-2357.
Engel T., et al., "Hippocampal Neuronal Subpopulations are Differentially Affected in Double Transgenic Mice Overexpressing Frontotemporal Dementia and Parkinsonism Linked to Chromosome 17 Tau and Glycogen Synthase Kinase-3Beta," Neuroscience, 2008, vol. 157 (4), pp. 772-780.
Infante J., et al., "Synergistic Effect of Two Oxidative Stress-Related Genes (Heme Oxygenase-1 and Gsk3B) on the Risk of Parkinson S Disease," European Journal of Neurology, 2010, vol. 17 (5), pp. 760-762.
Koh S.H., et al., "Role of Glycogen Synthase Kinase-3 in I-DOPA Induced neurotoxicity," Expert Opinion on Drug Metabolism & Toxicology, 2009, vol. 5 (11), pp. 1359-1368.
Kwok J.B.J., et aL, "GSK3B Polymorphisms Alter Transcription and Splicing in Parkinson's Disease," Annals of Neurology, 2005, vol. 58 (6), pp. 829-839.
Medina M., et al., "Glycogen Synthase Kinase-3 (GSK-3) Inhibitors for the Treatment of Alzheimer's Disease," Current Pharmaceutical Design, 2010, vol. 16 (25), pp. 2790-2798.

\* cited by examiner

HETEROCYCLIC COMPOUNDS AND THEIR USE AS GLYCOGEN SYNTHASE KINASE 3 INHIBITORS

CROSS-REFERENCE TO RELATED APPLICATIONS

This is a divisional of U.S. patent application Ser. No. 12/446,233, filed on Jun. 16, 2009, which is a U.S. national stage entry of International Patent Application No. PCT/EP2007/061231, filed on Oct. 19, 2007, which claims priority to U.S. Patent Application No. 60/936,837, filed on Jun. 22, 2007, and European Patent Application No. 06022094.4, filed on Oct. 21, 2006, the contents of all of which are fully incorporated herein by reference.

TECHNICAL FIELD

The present invention relates to novel urea compounds which are useful for inhibiting glycogen synthase kinase 3 (GSK-3), methods of making the compounds, compositions containing the compounds, and methods of treatment using the compounds.

BACKGROUND OF THE INVENTION

Glycogen synthase kinase-3 (GSK-3) is a serine/threonine kinase encoded by two isoforms, GSK-3α and GSK-3β with molecular weights of 51 and 47 kDa, respectively. These share 97% sequence similarity in their kinase catalytic domains. The GSK-3α isoform has an extended glycine-rich N-terminal tail. A minor splice variant of GSK-3β has been identified (expressed at ~15% of total) with a 13 amino acid insert within the kinase domain. This variant had a reduced activity towards tau. GSK-3 is highly conserved throughout evolution, and found in all mammalians thus far with high homology in the kinase domain. Both isoforms are ubiquitously expressed in mammalian tissues, including the brain. Pharmacological GSK-3 inhibitors are not able to selectively inhibit one of the isoforms.

GSK-3β plays an important role in the control of metabolism, differentiation and survival. It was initially identified as an enzyme able to phosphorylate and hence inhibit glycogen synthase. Subsequently, it was recognised that GSK-3β was identical to tau protein kinase 1 (TPK1), an enzyme that phosphorylates tau protein in epitopes that are also found to be hyperphosphorylated in Alzheimer's disease and in several taupathies.

Interestingly, protein kinase B (AKT) phosphorylation of GSK-3β results in a loss of kinase activity, and it has been proposed that this inhibition may mediate some of the effects of neurotrophic factors. Moreover, phosphorylation of β-catenin (a protein involved in cell survival) by GSK-3β, results in its degradation by an ubiquitinilation dependent proteasome pathway.

Therefore it appears that inhibition of GSK-3β activity may result in neurotrophic activity. There is evidence that lithium, an uncompetitive inhibitor of GSK-3β, enhances neuritogenesis in some models and can also increase neuronal survival, through the induction of survival factors such as Bcl-2 and the inhibition of the expression of proapoptotic factors such as P53 and Bax.

Further studies have shown that β-amyloid increases GSK-3β activity and tau protein phosphorylation. Moreover, this hyperphosphorylation as well as the neurotoxic effects of β-amyloid are blocked by lithium chloride and by a GSK-3β antisense mRNA. These observations taken together suggest that GSK-3β may be the link between the two major pathological processes in Alzheimer's disease: abnormal APP (Amyloid Precursor Protein) processing and tau protein hyperphosphorylation.

These experimental observations indicate that compounds which modulate the GSK-3β activity may find application in the treatment of the neuropathological consequences and the cognitive and attention deficits associated with Alzheimer's disease, as well as other acute and chronic neurodegenerative diseases. These include, but are not limited to: Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

GSK-3β may also have utility in the treatment of other diseases such as: Non-insulin dependent diabetes and obesity; osteoporosis; manic depressive illness; schizophrenia; alopecia; cancers such as breast cancer, non-small cell lung carcinoma, thyroid cancer, T or B-cell leukemia and several virus-induced tumors.

A review on GSK-3, its functions, its therapeutic potential and its possible inhibitors is given in "Glykogen Synthase Kinase 3 (GDK-3) and its inhibitors: Drug Discovery and Developments" by A. Martinez et al. (editors), John Wiley and Sons, 2006.

B. Barth et al. (Antiviral Chemistry & Chemotherapy 7 (6), 1996, 300-312) describe 6-alkyl substituted pyridazino[3,4-b][1,5]benzoxazepin-5-ones which are useful as inhibitors of HIV-1 reverse transcriptase. They also describe several pyridazino[3,4-b][1,5]benzoxazepin-5(6H)-ones being unsubstituted at the nitrogen as intermediates, namely pyridazino[3,4-b][1,5]benzoxazepin-5(6H)-one, 3-chloropyridazinobenzo[3,4-b][1,5]benzoxazepin-5(6H)-one, 3-chloro-8-trifluoromethylpyridazino[3,4-b][1,5]benzoxazepin-5(6H)-one, 3-chloro-8-methylpyridazino[3,4-b][1,5]benzoxazepin-5(6H)-one, 3-chloro-9-methylpyridazino[3,4-b][1,5]benzoxazepin-5(6H)-one, 3-chloro-8-methoxypyridazino[3,4-b][1,5]benzoxazepin-5(6H)-one and 3-chloro-8,10-dimethylpyridazinobenzo[3,4-b][1,5]benzoxazepin-5(6H)-one.

G. Heinisch et al. (Arch. Pharm. Pharm. Med. Chem. 2000, 333, 231-240) describe pyridazinobenzo[3,4-b][1,5]benzoxazepin-5(6H)-ones being unsubstituted at the nitrogen as intermediates in the synthesis of the corresponding N-alkyl derivatives, namely 3-chloropyridazinobenzo[3,4-b][1,5]benzoxazepin-5(6H)-one, 3,8-dichloropyridazino[3,4-b][1,5]benzoxazepin-5(6H)-one, 3-chloro-8-methylpyridazino[3,4-b][1,5]benzoxazepin-5(6H)-one and 3-chloro-9-methylpyridazino[3,4-b][1,5]benzoxazepin-5(6H)-one.

I. Ott et al. (J. Med. Chem. 2004, 47, 4627-4630) describe 6-alkyl substituted pyridazinobenzo[3,4-b][1,5]benzoxazepin-5-ones which are useful as Multidrug-Resistance Modulating agents in tumor therapy. They also describe several pyridazinobenzo[3,4-b][1,5]benzoxazepin-5(6H)-ones being unsubstituted at the nitrogen as intermediates, e.g. 3-chloro-9-trifluoromethylpyridazino[3,4-b][1,5]benzoxazepin-5(6H)-one.

G. Heinisch et al. (Arch. Pharm. Pharm. Med. Chem. 1997, 330, S. 29-34 and Heterocycles 1997, 45, 673-682) describe inter alia 3-chloro-8-nitro-11-propyl-pyridazino[3,4-b][1,5]benzodiazepin-5-one.

SUMMARY OF THE INVENTION

The object of the present invention is to provide compounds which modulate the GSK-3β activity, in particular compounds which have an inhibitory activity on GSK-3β and which thus are useful as an active ingredient of a composition for preventive and/or therapeutic treatment of a disease caused by abnormal GSK-3β activity, especially of neurodegenerative diseases. More specifically, the goal is to provide novel compounds useful as an active ingredient of a composition that enables prevention and/or treatment of neurodegenerative diseases such as Alzheimer's disease.

It was surprisingly found that the problem is solved by providing a heterocyclic compound of the general formula (I) (the symbol "C" in the monocyclic ring of formula (I) is only part of the numbering system and represents no chemical meaning by itself)

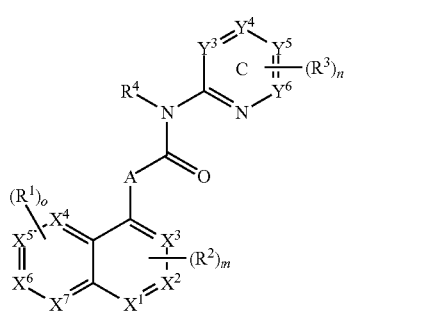

the stereoisomers, prodrugs and/or physiologically tolerated acid addition salts thereof, wherein A is selected from the group consisting of $CH_2$, NH, N—$C_1$-$C_4$-alkyl, N-halogenated (preferably fluorinated)-$C_1$-$C_4$-alkyl and $CR_A^1 R_A^2$, with $R_A^1$ and $R_A^2$ independently of one another are selected from the group consisting of H, $C_1$-$C_2$-alkyl halogenated (preferably fluorinated) $C_1$-$C_2$-alkyl, $NH_2$ and OH, preferably $R_A^1$ and $R_A^2$ independently of one another are selected from the group consisting of H, $C_1$-$C_2$-alkyl, halogenated (preferably fluorinated) $C_1$-$C_2$-alkyl, $NH_2$ and OH with the proviso that at least one of $R_A^1$ and $R_A^2$ is methyl or halogenated (preferably fluorinated) methyl, more preferably $R_A^1$ and $R_A^2$ are independently of one another selected from the group consisting of methyl and halogenated (preferably fluorinated) methyl;

$X^1$, and $X^2$ are independently of each other selected from the group consisting of CH, $CR^2$ and N;

$X^3$ is selected from the group consisting of CH, $CR^2$ and N;

$X^4$, $X^5$, $X^6$ and $X^7$ are independently of each other selected from the group consisting of C, CH, $CR^1$ and N, with the proviso that at least one of $X^1$, $X^2$, $X^3$, $X^4$, $X^5$, $X^6$, and $X^7$ is N, preferably with the proviso that at least $X^1$ of the group consisting of $X^1$, $X^2$, $X^3$, $X^4$, $X^5$, $X^6$, and $X^7$ is N;

$Y^3$, $Y^4$, $Y^5$ and $Y^6$ are independently of each other selected from the group consisting of a C, CH, $CR^3$ and N resulting in a 6-membered ring C; or one of $Y^3$, $Y^4$, $Y^5$ and $Y^6$ is part of the bridging bound between its two neighbour atoms resulting in a 5-membered ring C; or with $Y^5$=$Y^6$=C then $Y^5$ and $Y^6$ can form together with the 5- or 6-membered ring C a fused cyclic ring having 5- or 6-ring members including $Y^5$ and $Y^6$ as ring members and comprising C-atoms as ring members or instead of a C-atom ring member can contain 0, 1, 2 or 3 heteroatom ring members being independently of each other selected from the group consisting of N, O and S, where the fused ring system can be substituted with 1, 2 or 3 residues $R^3$ independently of each other having a meaning as defined below;

preferably with the proviso that at least one of $Y^3$, $Y^4$, $Y^5$ and $Y^6$ is N, in particular with the proviso that at least $Y^4$ of the group consisting of $Y^3$, $Y^4$, $Y^5$ and $Y^6$ is N and especially wherein $Y^4$ is N and the moieties $Y^3$, $Y^5$ and $Y^6$ are CH or $CR^3$;

n is the number of residues $R^3$ and is selected from 0, 1, 2, 3 or 4;

m is the number of residues $R^2$ and is selected from 0, 1 or 2;

o is the number of residues $R^1$ and is selected from 0, 1, 2, 3 or 4;

$R^1$, $R^3$ are independently of each other and independently of each occurrence selected from the group consisting of $NH_2$, NH—$C_1$-$C_6$-alkyl, $NR^a R^b$, OH, =O, $C_1$-$C_6$-alkoxy, $C_1$-$C_6$-haloalkoxy, halogen, $C_1$-$C_4$-alkyl, $C_3$-$C_7$-cycloalkyl, $C_2$-$C_4$-alkenyl, halogenated (preferably fluorinated) $C_1$-$C_4$-alkyl, halogenated (preferably fluorinated) $C_3$-$C_7$-cycloalkyl, halogenated (preferably fluorinated) $C_2$-$C_4$-alkenyl, formyl, $C_1$-$C_6$-alkylcarbonyl, $C_1$-$C_6$-alkyl-$NR^a R^b$ and an aromatic radical Ar, which is selected from the group consisting of phenyl and a 5- or 6-membered N- or C-bound heteroaromatic radical, comprising 1 nitrogen atom as ring member and 0, 1, 2 or 3 further heteroatoms, independently selected from O, S and N, as ring members, wherein Ar is unsubstituted or carries one or two radicals $R^{1a}$;

$R^2$ is independently of its occurrence selected from the group consisting of halogen, CN, $C_1$-$C_6$-alkyl, halogenated (preferably fluorinated) $C_1$-$C_6$-alkyl, $NR^a R^b$; or for m=2 or 3 two of $R^2$ at $X^2$ and $X^3$ can form together a fused 5- or 6-membered aliphatic cyclic ring which may contain 1 or 2 heteroatoms as ring members selected from the group consisting of N, O and S and which can be substituted with 1, 2 or 3 residues $R^3$ independently of each other having a meaning as defined above $R^{1a}$ is independently of each other and independently of its occurrence selected from the group consisting of halogen, $C_3$-$C_6$-cycloalkyl, $C_1$-$C_6$-alkoxy, halogenated (preferably fluorinated) $C_1$-$C_6$-alkyl, halogenated (preferably fluorinated) $C_3$-$C_6$-cycloalkyl, halogenated (preferably fluorinated) $C_1$-$C_6$-alkoxy, $NR^a R^b$, 1-aziridinyl, azetidin-1-yl, pyrrolidin-1-yl, piperidin-1-yl, morpholin-4-yl and homopiperidin-1-yl, a phenyl group or an aromatic 5- or 6-membered C-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or substituted by 1, 2, 3 or 4 radicals selected from halogen, cyano, $C_1$-$C_4$-alkyl, halogenated (preferably fluorinated) $C_1$-$C_4$-alkoxy and halogenated (preferably fluorinated) $C_1$-$C_4$-alkoxy;

$R^a$, $R^b$ are independently selected from the group consisting of H, $C_1$-$C_4$-alkyl, halogenated (preferably fluorinated) $C_1$-$C_4$-alkyl and $C_1$-$C_4$-alkoxy or may form, together with the nitrogen atom to which there bound, a 4-, 5-, 6- or 7-membered saturated or unsaturated N-heterocyclic ring, which may carry 1 further heteroatom selected from the group consisting of O, S and N as a ring member;

R[4] is selected from the group consisting of H, $C_1$-$C_4$-alkyl, and halogenated (preferably fluorinated) $C_1$-$C_6$-alkyl.

Thus, the present invention relates to compounds of the formula I as defined herein and in the claims, to the stereoisomers, prodrugs and/or physiologically tolerated acid addition salts thereof.

For the purpose of the invention, in the general formula (I) the ring atoms $X^5$ and $X^6$ are connected by a double bound (symbolized by "." or "=") to thereby form part of an aromatic bicyclic ring system consisting of 10 atoms as ring members.

As pointed out above, n is the number of residues $R^3$, m is the number of residues $R^2$ and o is the number of residues $R^1$. Thus, a skilled person will readily appreciate, that the number of those moieties $Y^3$, $Y^4$, $Y^5$ and $Y^6$ which are C—$R^3$ corresponds to the integer n. Likewise, a skilled person will readily appreciate, that the number of those moieties $X^1$, $X^2$ and $X^3$ which are C—$R^2$ corresponds to the integer m and that the number of those moieties $X^4$, $X^5$, $X^6$, and $X^7$ which are C—$R^1$ corresponds to the integer o.

According to a further aspect of the present invention, a heterocyclic compound of the general formula (I) (the symbol "C" in the monocyclic ring of formula (I) is only part of the numbering system and represents no chemical meaning by itself)

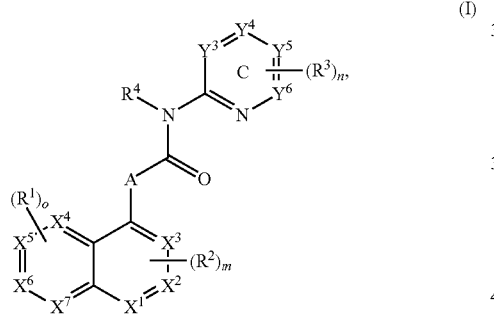

(I)

the stereoisomers, prodrugs and/or physiologically tolerated acid addition salts thereof are provided, wherein A is selected from the group consisting of $CH_2$, NH, N—$C_1$-$C_4$-alkyl, N-halogenated (preferably fluorinated)-$C_1$-$C_4$-alkyl and $CR_A^1R_A^2$, with $R_A^1$ and $R_A^2$ independently of one another are selected from the group consisting of H, halogenated (preferably fluorinated) $C_1$-$C_2$-alkyl, $NH_2$ and OH, preferably $R_A^1$ and $R_A^2$ independently of one another are selected from the group consisting of H, $C_1$-$C_2$-alkyl, halogenated (preferably fluorinated) $C_1$-$C_2$-alkyl, $NH_2$ and OH with the proviso that at least one of $R_A^1$ and $R_A^2$ is methyl or halogenated (preferably fluorinated) methyl, more preferably $R_A^1$ and $R_A^2$ are independently of one another selected from the group consisting of methyl and halogenated (preferably fluorinated) methyl;

$X^1$ is N;

$X^2$ is selected from the group consisting of CH, $CR^2$ and N;

$X^3$ is selected from the group consisting of CH and $CR^2$;

$X^4$, $X^5$, $X^6$ and $X^7$ are independently of each other selected from the group consisting of C, CH, $CR^1$ and N, with the proviso that at least one of $X^1$, $X^2$, $X^3$, $X^4$, $X^5$, $X^6$, and $X^7$ is N;

$Y^3$, $Y^4$, $Y^5$ and $Y^6$ are independently of each other selected from the group consisting of a C, CH, $CR^3$ and N resulting in a 6-membered ring C; or one of $Y^3$, $Y^4$, $Y^5$ and $Y^6$ is part of the bridging bound between its two neighbour atoms resulting in a 5-membered ring C; or with $Y^5$=$Y^6$=C then $Y^5$ and $Y^6$ can form together with the 5- or 6-membered ring C a fused cyclic ring having 5- or 6-ring members including $Y^5$ and $Y^6$ as ring members and comprising C-atoms as ring members or instead of a C-atom ring member 0, 1, 2 or 3 heteroatom ring members being independently of each other selected from the group consisting of N, O and S, where the fused ring system can be substituted with 1, 2 or 3 residues $R^3$ independently of each other having a meaning as defined below;

preferably with the proviso that at least one of $Y^3$, $Y^4$, $Y^5$ and $Y^6$ is N, in particular with the proviso that at least $Y^4$ of the group consisting of $Y^3$, $Y^4$, $Y^5$ and $Y^6$ is N and especially wherein $Y^4$ is N and the moieties $Y^3$, $Y^5$ and $Y^6$ are CH or $CR^3$;

n is the number of residues $R^3$ and is selected from 0, 1, 2, 3 or 4;

m is the number of residues $R^2$ and is selected from 0, 1 or 2;

o is the number of residues $R^1$ and is selected from 0, 1, 2, 3 or 4;

$R^1$, $R^3$ are independently of each other and independently of each occurrence selected from the group consisting of $NH_2$, NH—$C_1$-$C_6$-alkyl, $NR^aR^b$, OH, =O, $C_1$-$C_6$-alkoxy, $C_1$-$C_6$-haloalkoxy, halogen, $C_1$-$C_4$-alkyl, $C_3$-$C_7$-cycloalkyl, $C_2$-$C_4$-alkenyl, fluorinated $C_1$-$C_4$-alkyl, fluorinated $C_3$-$C_7$-cycloalkyl, fluorinated $C_2$-$C_4$-alkenyl, formyl, $C_1$-$C_6$-alkylcarbonyl, $C_1$-$C_6$-alkyl-$NR^aR^b$ and an aromatic radical Ar, which is selected from the group consisting of phenyl and a 5- or 6-membered N- or C-bound heteroaromatic radical, comprising 1 nitrogen atom as ring member and 0, 1, 2 or 3 further heteroatoms, independently selected from O, S and N, as ring members, wherein Ar is unsubstituted or carries one or two radicals $R^{1a}$;

$R^2$ is independently of its occurrence selected from the group consisting of halogen, CN, $C_1$-$C_6$-alkyl, fluorinated $C_1$-$C_6$-alkyl, $NR^aR^b$;

$R^{1a}$ is independently of each other and independently of its occurrence selected from the group consisting of halogen, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^aR^b$, 1-aziridinyl, azetidin-1-yl, pyrrolidin-1-yl, piperidin-1-yl, morpholin-4-yl and homopiperidin-1-yl, a phenyl group or an aromatic 5- or 6-membered C-bound heteroaromatic radical comprising 1 nitrogen atom as ring member and 0, 1, 2 or 3 further heteroatoms independently selected from O, S and N, as ring members, wherein phenyl and the heteroaromatic radical are, independently of each other, unsubstituted or substituted by 1, 2, 3 or 4 radicals selected from halogen, cyano, $C_1$-$C_4$-alkyl, fluorinated $C_1$-$C_4$-alkyl, $C_1$-$C_4$-alkoxy and fluorinated $C_1$-$C_4$-alkoxy;

$R^a$, $R^b$ are independently selected from the group consisting of H, $C_1$-$C_4$-alkyl, fluorinated $C_1$-$C_4$-alkyl and $C_1$-$C_4$-alkoxy or may form, together with the nitrogen atom to which there bound, a 4-, 5-, 6- or 7-membered saturated or unsaturated N-heterocyclic ring, which may carry 1 further heteroatom selected from the group consisting of O, S and N as a ring member;

R⁴ is selected from the group consisting of H, $C_1$-$C_4$-alkyl, and halogenated (preferably fluorinated) $C_1$-$C_6$-alkyl.

According to a further embodiment of the present invention, a heterocyclic compound of the general formula (I) (the symbol "C" in the monocyclic ring of formula (I) is only part of the numbering system and represents no chemical meaning by itself)

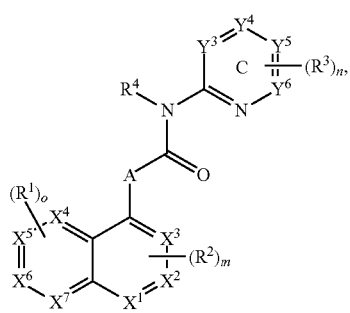
(I)

the stereoisomers, prodrugs and/or physiologically tolerated acid addition salts thereof are provided, wherein A, $R^1$, $R^2$, $R^3$, $R^4$, m, n, o, $X^1$, $X^2$, $X^4$, $X^5$, $X^6$, $X^7$, $Y^3$, $Y^4$, $Y^5$, and $Y^6$ have the same meaning, unless otherwise stated, as given herein or as defined in claim 1 or 15, wherein $X^3$ is CH.

According to a further embodiment of the present invention, a heterocyclic compound of the general formula (I) (the symbol "C" in the monocyclic ring of formula (I) is only part of the numbering system and represents no chemical meaning by itself)

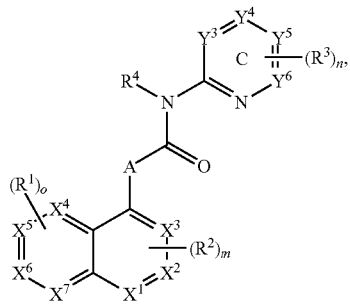
(I)

the stereoisomers, prodrugs and/or physiologically tolerated acid addition salts thereof are provided, wherein A, $R^1$, $R^2$, $R^3$, $R^4$, m, n, o, $X^1$, $X^2$, $X^3$, $X^4$, $X^5$, $X^6$, $X^7$, $Y^3$, $Y^5$, and $Y^6$ have the same meaning, unless otherwise stated, as defined herein or in any one of claim 1 to 15, wherein $Y^4$ is N.

According to a further embodiment of the present invention, a heterocyclic compound of the general formula (I) (the symbol "C" in the monocyclic ring of formula (I) is only part of the numbering system and represents no chemical meaning by itself)

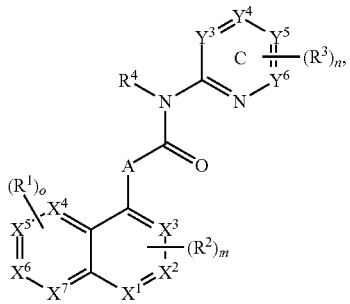
(I)

the stereoisomers, prodrugs and/or physiologically tolerated acid addition salts thereof are provided, wherein A, $R^1$, $R^2$, $R^3$, R4, m, n, o, $X^1$, $X^2$, $X^3$, $X^4$, $X^5$, $X^6$, $X^7$, $Y^3$, $Y^4$, $Y^5$, and $Y^6$ have the same meaning, unless otherwise stated, as defined herein or in any one of claims 1 to 15, wherein $R^3$, if present, is halogen.

According to a further embodiment of the present invention, a heterocyclic compound of the general formula (I) (the symbol "C" in the monocyclic ring of formula (I) is only part of the numbering system and represents no chemical meaning by itself)

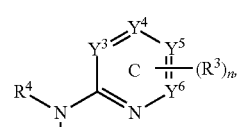

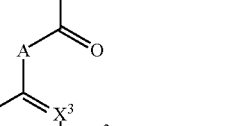
(I)

the stereoisomers, prodrugs and/or physiologically tolerated acid addition salts thereof are provided, wherein A, $R^1$, $R^2$, $R^4$, m, o, $X^1$, $X^2$, $X^3$, $X^4$, $X^5$, $X^6$, $X^7$, $Y^3$, $Y^4$, $Y^5$, and $Y^6$ have the same meaning, unless otherwise stated, as defined herein or in any one of claims 1 to 15, wherein n is 0 or 1 and wherein $R^3$ is halogen (or wherein n is 1 and wherein $R^3$ is H or halogen).

According to a further embodiment of the present invention, a heterocyclic compound of the general formula (I) (the symbol "C" in the monocyclic ring of formula (I) is only part of the numbering system and represents no chemical meaning by itself)

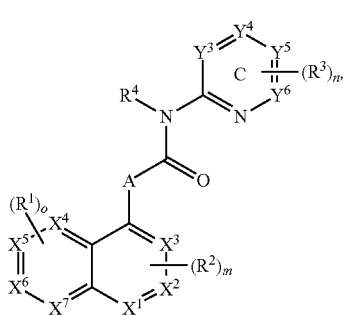

(I)

the stereoisomers, prodrugs and/or physiologically tolerated acid addition salts thereof are provided, wherein A, $R^1$, $R^3$, $R^4$, n, o, $X^1$, $X^2$, $X^3$, $X^4$, $X^5$, $X^6$, $X^7$, $Y^3$, $Y^4$, $Y^5$, and $Y^6$ have the same meaning, unless otherwise stated, as defined herein or in any one of claims 1 to 15, wherein m is 0 or 1 and wherein $R^2$ is halogen (or wherein m is 1 and wherein $R^2$ is H or halogen).

According to a further embodiment of the present invention, a heterocyclic compound of the general formula I (the symbol "C" in the monocyclic ring of formula (I) is only part of the numbering system and represents no chemical meaning by itself)

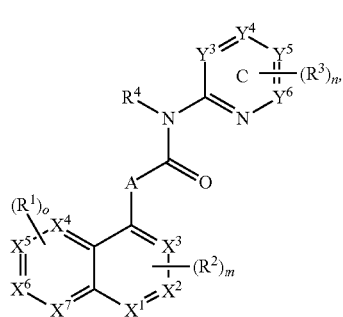

(I)

the stereoisomers, prodrugs and/or physiologically tolerated acid addition salts thereof are provided, wherein A, $R^1$, $R^2$, $R^3$, $R^4$, m, n, $X^1$, $X^2$, $X^3$, $X^4$, $X^6$, $X^7$, $Y^3$, $Y^4$, $Y^5$, and $Y^6$ have the same meaning, unless otherwise stated, as defined herein or in any one of claims 1 to 15, wherein o is selected from 0, 1, 2, 3 or 4, in particular 1, 2, 3 or 4;

$X^5$ CH or $CR^1$ in particular $CR^1$;

$R^1$ if present, at least is located at $X^5$ and is independently of its occurrence selected from the group consisting of halogen, $C_1$-$C_4$-alkyl and halogenated (preferably fluorinated) $C_1$-$C_4$-alkyl.

According to a further embodiment of the present invention a heterocyclic compound of the general formula I (the symbol "C" in the monocyclic ring of formula (I) is only part of the numbering system and represents no chemical meaning by itself)

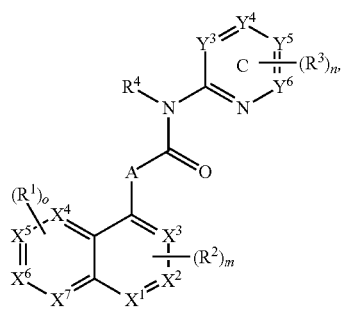

(I)

the stereoisomers, prodrugs and/or physiologically tolerated acid addition salts thereof are provided, wherein A, $R^2$, $R^3$, $R^4$, m, n, $X^1$, $X^2$, $X^3$, $X^4$, $X^5$, $X^6$, $X^7$, $Y^3$, $Y^4$, $Y^5$, and $Y^6$ have the same meaning, unless otherwise stated, as defined herein or in any one of claims 1 to 15, wherein o is 0 or 1;

$R^1$ if present, is selected from the group consisting of halogen, $C_1$-$C_4$-alkyl and halogenated (preferably fluorinated) $C_1$-$C_4$-alkyl (or wherein o is 1 and $R^1$ is selected from the group consisting of halogen, $C_1$-$C_4$-alkyl and halogenated (preferably fluorinated) $C_1$-$C_4$-alkyl).

According to a further embodiment of the present invention, a heterocyclic compound of the general formula I (the symbol "C" in the monocyclic ring of formula (I) is only part of the numbering system and represents no chemical meaning by itself)

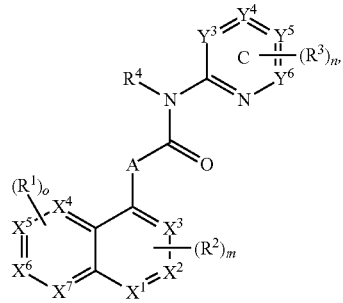

(I)

the stereoisomers, prodrugs and/or physiologically tolerated acid addition salts thereof are provided, wherein $R^1$, $R^2$, $R^3$, $X^2$, $X^3$, $X^4$, $X^5$, $X^6$, $X^7$, $Y^3$, $Y^4$, $Y^5$, and $Y^6$ have the same meaning, unless otherwise stated, as defined herein or in any one of claims 1 to 15, wherein A is NH;

$X^1$ is N;

$R^4$ is H;

o is 0 or 1;

m is 0 or 1;

n is 0 or 1.

According to a further embodiment of the present invention a heterocyclic compound of the general formula I (the symbol "C" in the monocyclic ring of formula (I) is only part of the numbering system and represents no chemical meaning by itself)

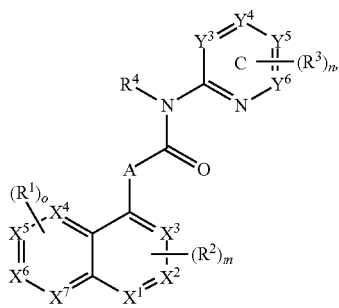

the stereoisomers, prodrugs and/or physiologically tolerated acid addition salts thereof are provided, wherein $R^1$, $R^2$, $R^3$, $Y^3$, $Y^5$, and $Y^6$ have the same meaning, unless otherwise stated, as defined herein or in any one of claims 1 to 13, wherein A is NH;
$X^1$ is N;
$X^2$, $X^3$ is independently of each other CH or $CR^2$;
$Y^4$ is N;
$X^4$, $X^5$, $X^6$, $X^7$ are independently of each other CH or $CR^1$;
$R^4$ is H;
o is 0 or 1;
m is 0 or 1;
n is 0 or 1.

According to a further embodiment of the present invention a heterocyclic compound of the general formula I (the symbol "C" in the monocyclic ring of formula (I) is only part of the numbering system and represents no chemical meaning by itself)

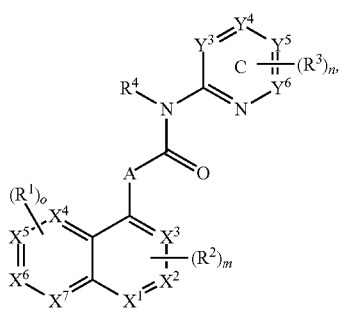

the stereoisomers, prodrugs and/or physiologically tolerated acid addition salts thereof are provided, wherein $R^1$, $R^2$ and $R^3$ have the same meaning, unless otherwise stated, as defined herein or in any one of claims 1 to 14, wherein A is NH;
$X^1$ is N;
$X^2$, $X^3$ is independently of each other CH or $CR^2$;
$Y^4$ is N;
$X^4$, $X^5$, $X^6$, $X^7$ are independently of each other CH or $CR^1$;
$Y^3$, $Y^5$, $Y^6$ are independently of each other CH or $CR^3$;
$R^4$ is H;
o is 0 or 1, in particular 1;
m is 0 or 1;
n is 0 or 1.

According to a further embodiment of the present invention a heterocyclic compound of the general formula I (the symbol "C" in the monocyclic ring of formula (I) is only part of the numbering system and represents no chemical meaning by itself)

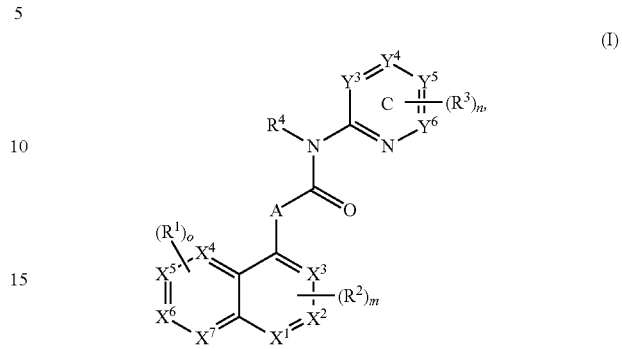

selected from the following compounds:
1-Pyrazin-2-yl-3-(6-trifluoromethyl-quinolin-4-yl)-urea
1-Pyrazin-2-yl-3-(7-trifluoromethyl-quinolin-4-yl)-urea
1-Pyrazin-2-yl-3-(8-trifluoromethyl-quinolin-4-yl)-urea
1-(2-Methyl-quinolin-4-yl)-3-pyrazin-2-yl-urea
1-Pyrazin-2-yl-3-quinolin-4-yl-urea
1-Pyrazin-2-yl-3-(2-trifluoromethyl-quinolin-4-yl)-urea
1-(6-Bromo-quinolin-4-yl)-3-pyrazin-2-yl-urea
1-Methyl-1-pyrazin-2-yl-3-(6-trifluoromethyl-quinolin-4-yl)-urea
1-Isoquinolin-1-yl-3-pyrazin-2-yl-urea
1-Pyrazin-2-yl-3-quinolin-8-yl-urea
1-Isoquinolin-8-yl-3-pyrazin-2-yl-urea
1-Pyrazin-2-yl-3-quinolin-5-yl-urea
1-Isoquinolin-5-yl-3-pyrazin-2-yl-urea
1-Isoquinolin-4-yl-3-pyrazin-2-yl-urea
1-Pyrazin-2-yl-3-(1,2,3,4-tetrahydro-acridin-9-yl)-urea
1-(Pyrazin-2-yl)-3-(pyridin-4-yl)urea
1-(Quinolin-4-yl)-3-(pyrazin-2-yl)urea
1-(8-Fluoroquinolin-4-yl)-3-(pyrazin-2-yl)urea
1-(7-Iodoquinolin-4-yl)-3-(pyrazin-2-yl)urea
1-(7-Bromoquinolin-4-yl)-3-(pyrazin-2-yl)urea
1-(Pyridin-2-yl)-3-(7-(trifluoromethyl)quinolin-4-yl)urea
1-(8-Methylquinolin-4-yl)-3-(pyrazin-2-yl)urea
1-(8-Chloroquinolin-4-yl)-3-(pyrazin-2-yl)urea
1-(6-Morpholinopyridin-2-yl)-3-(8-(trifluoromethyl)quinolin-4-yl)urea
1-(8-Iodoquinolin-4-yl)-3-(pyrazin-2-yl)urea
1-(3-Bromoquinolin-4-yl)-3-(pyrazin-2-yl)urea
1-(6,8-Difluoroquinolin-4-yl)-3-(pyrazin-2-yl)urea
1-(8-Bromoquinolin-4-yl)-3-(pyrazin-2-yl)urea
1-(1,5-Naphthyridin-4-yl)-3-(pyrazin-2-yl)urea
1-(5-Chloro-1H-1,2,3-triazol-4-yl)-3-(7-(trifluoromethyl)quinolin-4-yl)urea the stereoisomers, prodrugs and/or physiologically tolerated acid addition salts thereof; are provided.

According to a further aspect, the present invention relates to a heterocyclic compound of the general formula I (the symbol "C" in the monocyclic ring of formula (I) is only part of the numbering system and represents no chemical meaning by itself)

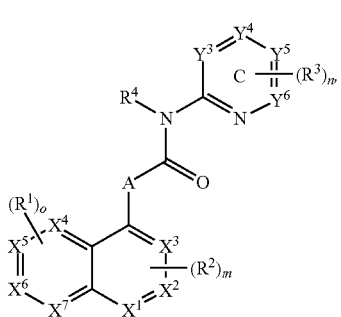

(I)

the stereoisomers, prodrugs and/or physiologically tolerated acid addition salts thereof, wherein A, $R^1$, $R^2$, $R^3$, $R^4$, m, n, o, $X^1$, $X^2$, $X^3$, $X^4$, $X^5$, $X^6$, $X^7$, $Y^3$, $Y^4$, $Y^5$, and $Y^6$ have the same meaning as defined herein or in any one of claims 1 to 15, for use as a medicament.

According to a further aspect, the present invention relates to the use of at least one heterocyclic compound of the general formula I (the symbol "C" in the monocyclic ring of formula (I) is only part of the numbering system and represents no chemical meaning by itself)

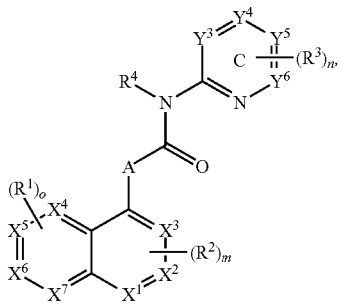

(I)

the stereoisomers, prodrugs and/or physiologically tolerated acid addition salts thereof, wherein A, $R^1$, $R^2$, $R^3$, $R^4$, m, n, o, $X^1$, $X^2$, $X^3$, $X^4$, $X^5$, $X^6$, $X^7$, $Y^3$, $Y^4$, $Y^5$, and $Y^6$ have the same meaning as defined herein or in any one of claims 1 to 15, for preparation of a medicament for the treatment of a disease susceptible to the treatment with a compound that modulates, preferably inhibits the activity of glycogen synthase kinase According to a further aspect, the present invention relates to the use of at least one heterocyclic compound of the general formula I (the symbol "C" in the monocyclic ring of formula (I) is only part of the numbering system and represents no chemical meaning by itself)

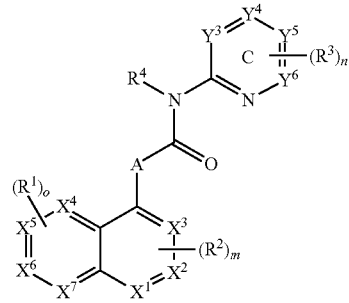

(I)

the stereoisomers, prodrugs and/or physiologically tolerated acid addition salts thereof, wherein A, $R^1$, $R^2$, $R^3$, $R^4$, m, n, o, $X^1$, $X^2$, $X^3$, $X^4$, $X^5$, $X^6$, $X^7$, $Y^3$, $Y^4$, $Y^5$, and $Y^6$ have the same meaning as defined herein or in any one of claims 1 to 15, for preparation of a medicament for the treatment of a disease susceptible to the treatment with a compound that inhibits the activity of glycogen synthase kinase 3β, wherein said heterocyclic compound has an $IC_{50}$ level for inhibitory activity on glycogen synthase kinase 3β of $IC_{50}<1$ μMol.

According to a further aspect, the present invention relates to a pharmaceutical composition comprising at least one compound of the formula I, wherein A, $R^1$, $R^2$, $R^3$, $R^4$, m, n, o, $X^1$, $X^2$, $X^3$, $X^4$, $X^5$, $X^6$, $X^7$, $Y^3$, $Y^4$, $Y^5$, and $Y^6$ have the same meaning as defined herein or in any one of claims 1 to 15, a stereoisomer, a prodrug and/or a physiologically tolerated acid addition salts thereof, optionally together with at least one physiologically acceptable carrier and/or auxiliary substance.

According to a further aspect, the present invention relates to a method for treating a medical disorder susceptible to treatment with a compound that modulates glycogen synthase kinase 3β activity, said method comprising administering an effective amount of at least one compound of the formula I, wherein A, $R^1$, $R^2$, $R^3$, $R^4$, m, n, o, $X^1$, $X^2$, $X^3$, $X^4$, $X^5$, $X^6$, $X^7$, $Y^3$, $Y^4$, $Y^5$, and $Y^6$ have the same meaning as defined herein or in any one of claims 1 to 15, a stereoisomer, a prodrugs and/or a physiologically tolerated acid addition salt thereof, to a subject in need thereof.

The medical disorder, which is susceptible to treatment with a compound that modulates glycogen synthase kinase 3β activity, is in particular a neurodegenerative disorder.

According to a further aspect, the present invention relates to the use of at least one compound of the formula I, wherein A, $R^1$, $R^2$, $R^3$, $R^4$, m, n, o, $X^1$, $X^2$, $X^3$, $X^4$, $X^5$, $X^6$, $X^7$, $Y^3$, $Y^4$, $Y^5$, and $Y^6$ have the same meaning as defined herein or in any one of claims 1 to 16, the stereoisomers, prodrugs and/or physiologically tolerated acid addition salts thereof, for the preparation of a pharmaceutical composition for the treatment of a medical disorder susceptible to treatment with a compound that modulates glycogen synthase kinase 3β activity, wherein the medical disorder is in particular a neurodegenerative disorder, is provided.

Therefore the present invention also relates to disubstituted urea compounds of the general formula I, and to their pharmacologically acceptable acid addition salts, except for the compounds already known.

The present invention also relates to a pharmaceutical composition which comprises at least one disubstituted urea compound of the formula (I) and/or at least one physiologically tolerated acid addition salt of (I), where appropriate together with physiologically acceptable carriers and/or auxiliary substances.

The present invention in particular relates to a method for treatment of neurodegenerative diseases caused by abnormal activity of GSK-3β and of the aforementioned diseases which comprises administering to a mammalian organism in need thereof an effective amount of a compound of the formula (I).

DETAILED DESCRIPTION OF THE INVENTION

According to the invention, the compounds of the general formula I having the meanings mentioned at the outset have a modulating, and in particular inhibitory activity against GSK-3β. Accordingly, the compounds of the present invention are useful for treatment of a medical disorder susceptible to treatment with a compound that modulates and in particular inhibits glycogen synthase kinase 3β activity. The term "treatment", as used herein includes preventive treatment and therapeutic treatment. Thus, these compounds are useful as an active ingredient for the preparation of a composition, which enables treatment of a disease caused by abnormal GSK-3β activity and more particularly of neurodegenerative diseases such as Alzheimer's disease. In addition, the compounds of the present invention are also useful for treatment of neurodegenerative diseases such as Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma. The compounds are also useful for treatment of other medical disorders susceptible to treatment with a compound that modulates and in particular inhibits glycogen synthase kinase 3β activity, such as non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

$C_1$-$C_4$ Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$ Alkyl is methyl or ethyl, $C_1$-$C_3$ alkyl is additionally n-propyl or isopropyl.

$C_1$-$C_6$ Alkyl is a straight-chain or branched alkyl group having from 1 to 6 carbon atoms. Examples include methyl, $C_2$-$C_4$ alkyl as mentioned above and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluorinated $C_1$-$C_6$ alkyl is a straight-chain or branched alkyl group having from 1 to 6, especially 1 to 4 carbon atoms (=fluorinated $C_1$-$C_4$ alkyl), in particular 1 to 3 carbon atoms (=fluorinated $C_1$-$C_3$ alkyl), wherein at least one, e.g. 1, 2, 3, 4 or all of the hydrogen atoms are replaced by a fluorine atom such as in fluoromethyl, difluoromethyl, trifluoromethyl, (R)-1-fluoroethyl, (S)-1-fluoroethyl, 2-fluoroethyl, 1,1-difluoroethyl, 2,2-difluoroethyl, 2,2,2-trifluoroethyl, 1,1,2,2-tetrafluoroethyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, (R)-2-fluoro-1-methylethyl, (S)-2-fluoro-1-methylethyl, (R)-2,2-difluoro-1-methylethyl, (S)-2,2-difluoro-1-methylethyl, (R)-1,2-difluoro-1-methylethyl, (S)-1,2-difluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

$C_1$-$C_6$ Alkoxy is a straight-chain or branched alkyl group having from 1 to 6, in particular 1 to 4 carbon atoms (=$C_1$-$C_4$ alkoxy), which is bound to the remainder of the molecule via an oxygen atom. Examples include methoxy, ethoxy, n-propoxy, isopropoxy, n-butoxy, 2-butoxy, iso-butoxy, tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$ alkoxy (which is also termed $C_1$-$C_6$ haloalkoxy), in particular fluorinated $C_1$-$C_6$ alkoxy (also termed $C_1$-$C_6$ fluoroalkoxy) is a straight-chain or branched alkoxy group having from 1 to 6, in particular 1 to 4 carbon atoms (=fluorinated $C_1$-$C_4$ alkoxy), wherein at least one, e.g. 1, 2, 3, 4 or all of the hydrogen atoms are replaced by a halogen atoms, in particular fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1, 2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_6$ Hydroxyalkyl is a straight-chain or branched alkyl group having from 1 to 6, especially 1 to 4 carbon atoms (=$C_1$-$C_4$ hydroxyalkyl), in particular 1 to 3 carbon atoms (=$C_1$-$C_3$ hydroxyalkyl), wherein one of the hydrogen atoms is replaced by a hydroxy group, such as in hydroxymethyl, 1- or 2-hydroxyethyl or 1-, 2- or 3-hydroxypropyl.

$C_1$-$C_6$ Hydroxyalkoxy is a straight-chain or branched alkoxy group having from 1 to 6, especially 1 to 4 carbon atoms (=$C_1$-$C_4$ hydroxyalkoxy), in particular 1 to 3 carbon atoms (=$C_1$-$C_3$ hydroxyalkoxy), wherein one of the hydrogen atoms is replaced by a hydroxy group, such as in 2-hydroxyethoxy or 3-hydroxypropyloxy.

$C_1$-$C_6$-Alkoxy-$C_1$-$C_6$-alkyl is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in methoxymethyl, 2-methoxyethyl, ethoxymethyl, 3-methoxypropyl, 3-ethoxypropyl and the like.

$C_1$-$C_6$-Alkoxy-$C_1$-$C_6$-alkoxy is a straight-chain or branched alkyl group having from 1 to 6, especially 1 to 4 carbon atoms, in particular 1 to 3 carbon atoms, wherein one of the hydrogen atoms is replaced by a $C_1$-$C_6$-alkoxy group, such as in 2-methoxyethoxy, ethoxymethoxy, 2-ethoxyethoxy, 3-methoxypropoxy, 3-ethoxypropoxy and the like.

$C_1$-$C_6$-Alkylcarbonyl is a straight-chain or branched alkyl group having from 1 to 6, especially 1 to 4 carbon atoms (=$C_1$-$C_4$ alkylcarbonyl), in particular 1 to 3 carbon atoms (=$C_1$-$C_3$ alkylcarbonyl), which is bound to the remainder of the molecule via a carbonyl group (CO), such as in acetyl and propionyl.

Fluorinated $C_1$-$C_6$-alkylcarbonyl is a straight-chain or branched alkyl group having from 1 to 6, especially 1 to 4 carbon atoms (=fluorinated $C_1$-$C_4$ alkylcarbonyl), in particular 1 to 3 carbon atoms (=fluorinated $C_1$-$C_3$ alkylcarbonyl), which is bound to the remainder of the molecule via a carbonyl group (CO), and wherein at least one of the remaining hydrogen atoms, e.g. 1, 2, 3, or 4 of the hydrogen atoms are replaced by a fluorine atom, such as in trifluoroacetyl and 3,3,3-trifluoropropionyl.

$C_1$-$C_6$-Alkoxycarbonyl is a straight-chain or branched alkoxy group having from 1 to 6, especially 1 to 4 carbon atoms (=$C_1$-$C_4$ alkoxycarbonyl), in particular 1 to 3 carbon atoms (=$C_1$-$C_3$ alkoxycarbonyl), which is bound to the remainder of the molecule via a carbonyl group (CO), such as in methoxycarbonyl, ethoxycarbonyl, propyloxycarbonyl, and isopropyloxycarbonyl.

Fluorinated $C_1$-$C_6$-alkoxycarbonyl is a straight-chain or branched alkoxy group having from 1 to 6, especially 1 to 4 carbon atoms (=fluorinated $C_1$-$C_4$ alkoxycarbonyl), in particular 1 to 3 carbon atoms (=fluorinated $C_1$-$C_3$ alkoxycarbonyl), which is bound to the remainder of the molecule via a carbonyl group (CO), and wherein at least one of the remaining hydrogen atoms, e.g. 1, 2, 3, or 4 of the hydrogen atoms are replaced by a fluorine atom, such as in fluormethoxycarbonyl, trifluoromethoxycarbonyl and 2,2,2-triflourethoxycarbonyl.

$C_1$-$C_6$-Alkylcarbonylamino is a straight-chain or branched alkyl group having from 1 to 6, especially 1 to 4 carbon atoms (=$C_1$-$C_4$ alkylcarbonylamino), in particular 1 to 3 carbon atoms (=$C_1$-$C_4$ alkylcarbonylamino), wherein one of the hydrogen atoms is replaced by a carbonylamino group (CO—NH—), such as in acetamido (acetylamino) ($CH_3CONH$—) and propionamido ($CH_3CH_2CONH$—).

Fluorinated $C_1$-$C_6$-alkylcarbonylamino is a straight-chain or branched alkyl group having from 1 to 6, especially 1 to 4 carbon atoms (=fluorinated $C_1$-$C_4$ alkylcarbonylamino), in particular 1 to 3 carbon atoms (=fluorinated $C_1$-$C_4$ alkylcarbonylamino), wherein one of the hydrogen atoms is replaced by a carbonylamino group (CO—NH—) and wherein at least one of the remaining hydrogen atoms, e.g. 1, 2, 3, or 4 of the hydrogen atoms are replaced by a fluorine atom, such as in trifluoroacetylamino and 3,3,3-trifluoropropionylamino.

$C_1$-$C_6$ Alkylthio (also termed as $C_1$-$C_6$-alkylsulfanyl) (or $C_1$-$C_6$-alkylsulfinyl or $C_1$-$C_6$-alkylsulfonyl, respectively) refer to straight-chain or branched alkyl groups having 1 to 6 carbon atoms, e.g. 1 to 4 carbon atoms, which are bound to the remainder of the molecule via a sulfur atom (or S(O) in case of alkylsulfinyl or $SO_2$ in case of alkylsulfonyl, respectively), at any bond in the alkyl group. Examples for $C_1$-$C_4$-alkylthio include methylthio, ethylthio, propylthio, isopropylthio, and n-butylthio. Examples for $C_1$-$C_4$-alkylsulfinyl include methylsulfinyl, ethylsulfinyl, propylsulfinyl, isopropylsulfinyl, and n-butylsulfinyl. Examples for $C_1$-$C_4$-alkylsulfonyl include methylsulfonyl, ethylsulfonyl, propylsulfonyl, isopropylsulfonyl, and n-butylsulfonyl.

Fluorinated $C_1$-$C_6$ alkylthio (also termed fluorinated $C_1$-$C_6$-alkylsulfanyl) is a straight-chain or branched alkylthio group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$ alkylsulfinyl is a straight-chain or branched alkylsulfinyl group having from 1 to 6, in particular 1 to 4 carbon atoms, wherein at least one, e.g. 1, 2, 3, 4 or all of the hydrogen atoms are replaced by fluorine atoms. Fluorinated $C_1$-$C_6$ alkylsulfonyl is a straight-chain or branched alkylsulfonyl group having from 1 to 6, in particular 1 to 4 carbon atoms, wherein at least one, e.g. 1, 2, 3, 4 or all of the hydrogen atoms are replaced by fluorine atoms.

$C_3$-$C_6$ Cycloalkyl is a cycloaliphatic radical having from 3 to 6 C atoms, such as cyclopropyl, cyclobutyl, cyclopentyl and cyclohexyl. The cycloalkyl radical may be unsubstituted or may carry 1, 2, 3 or 4 $C_1$-$C_4$ alkyl radicals, preferably a methyl radical. One alkyl radical is preferably located in the 1-position of the cycloalkyl radical, such as in 1-methylcyclopropyl or 1-methylcyclobutyl. Likewise, $C_3$-$C_4$ Cycloalkyl is a cycloaliphatic radical having from 3 to 4 C atoms, such as cyclopropyl, cyclobutyl and 1-methylcyclopropyl.

Fluorinated $C_3$-$C_6$ cycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a fluorine atoms such as in 1-fluorocyclopropyl, 2-fluorocyclopropyl, (S)— and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_2$-$C_6$-Alkenyl is a singly unsaturated hydrocarbon radical having 2, 3, 4, 5 or 6 C-atoms, e.g. vinyl, allyl (2-propen-1-yl), 1-propen-1-yl, 2-propen-2-yl, methallyl (2-methyl-prop-2-en-1-yl) and the like. $C_3$-$C_6$-Alkenyl is, in particular, allyl, 1-methyl prop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

Fluorinated $C_2$-$C_6$-alkenyl is a singly unsaturated hydrocarbon radical having 2, 3, 4, 5 or 6 C-atoms, I, wherein at least one, e.g. 1, 2, 3, 4 or all of the hydrogen atoms are replaced by a fluorine atoms such as in 1-fluorovinyl, 2-fluorovinyl, 2,2-fluorovinyl, 3,3,3-fluoropropenyl, 1,1-difluoro-2-propenyl, 1-fluoro-2-propenyl and the like.

$C_2$-$C_6$-Alkynyl is a hydrocarbon radical having a C—C-triple bond and 2, 3, 4, 5 or 6 C-atoms, e.g. ethynyl, propargyl, (2-propyn-1-yl), 1-propyn-1-yl, 2-butyn-1-yl 1-methyl-2-butyn-1-yl, 2-pentyn-1-yl, 2-hexyn-1-yl and the like.

$C_1$-$C_6$-Alkylene is a hydrocarbon bridging group having 1, 2, 3, 4, 5 or 6 carbon atoms, like methylene, ethylene, 1,2- and 1,3-propylene, 1,4-butylene and the like.

Examples of 5- or 6-membered heteroaromatic radicals include 2-, 3-, or 4-pyridyl, 2-, 4- or 5-pyrimidinyl, pyrazinyl, 3- or 4-pyridazinyl, 2- or 3-thienyl, 2- or 3-furyl, 2- or 3-pyrrolyl, 2-, 3- or 5-oxazolyl, 3-, 4- or 5-isoxazolyl, 2-, 3- or 5-thiazolyl, 3-, 4- or 5-isothiazolyl, 3-, 4- or 5-pyrazolyl, 2-, 4- or 5-imidazolyl, 2- or 5-[1,3,4]oxadiazolyl, 4- or 5-[1,2,3]oxadiazolyl, 3- or 5-[1,2,4]oxadiazolyl, 2- or 5-[1,3,4]thiadiazolyl, 2- or 5-[1,3,4]thiadiazolyl, 4- or 5-[1,2,3]thiadiazolyl, 3- or 5-[1,2,4]thiadiazolyl 1H-, 2H- or 3H-1,2,3-triazol-4-yl, 2H-triazol-3-yl, 1H-, 2H-, or 4H-1,2,4-triazolyl and 1H- or 2H-tetrazolyl.

Examples of fused saturated or unsaturated 5-, 6- or 7-membered carbocyclic rings include cyclopentano, 1,2-cyclopenteno, 2,3-cyclopenteno, 3,4-cyclopenteno, cyclohexano, 1,2-cyclohexeno, 2,3-cyclohexeno, 3,4-cyclohexeno, 1,2-cyclohexa-1,3-dieno, 2,3-cyclohexa-1,3-dieno, 3,4-cyclohexa-1,3-dieno, 4,5-cyclohexa-1,3-dieno, 5,6-cyclohexa-1,3-dieno, 1,2-cyclohexa-1,4-dieno, 1,2-cyclohexa-1,4-dieno, cycloheptano, 1,2-cyclohepteno, 2,3-cyclohepteno, 3,4-cyclohepteno, 1,2-cyclo-1,3-heptadieno and benzeno (benzo).

Examples for fused saturated or unsaturated 5-, 6- or 7-membered heterocyclic rings (as radicals $R^a$ comprise saturated or unsaturated, aromatic or non-aromatic heterocyclic rings. Examples therefore include fused 5- or 6-membered heteroaromatic radicals, such as thieno, furano, pyrrolo, pyrazolo, imidazolo, 1,2,3-triazolo, oxazolo, thiazolo, isoxazolo, isothiazolo, pyridino, pyrimidino, pyridazino, and also 5-, 6- or 7-membered saturated or mono-unsaturated heterocyclic rings di- and tetrahydrofurano, pyrrolino, pyrrolidino, oxopyrrolidino, pyrazolino, pyrazolidino, imidazolino, imidazolidino, oxazolino, oxazolidino, 2-oxo-oxazolidino, isoxazolino, isoxazolidino, piperidino, piperazino, morpholino, thiomorpholino, oxano, 1,4-dioxano and the like.

If $R^a$ and $R^b$ form together with N a 4-, 5-, 6- or 7-membered ring, examples for this type of radical comprise, apart from the above defined, 5- or 6-membered heteroaromatic radicals containing at least one N atom as ring member, azetidin-1-yl, azetin-1-yl, pyrrolin-1-yl, pyrrolidin-1-yl, pyrazolin-1-yl, pyrazolidin-1-yl, imidazolin-1-yl, imidazolidin-1-yl, oxazolin-1-yl, oxazolidin-1-yl, piperidin-1-yl, piperazin-1-yl, morpholin-4-yl and the like.

In formula I and also in formulae 1A, 1B and 1C, the variables A, $R^1$, $R^2$, $R^3$, $R^4$, m, n, o, $X^1$, $X^2$, $X^3$, $X^4$, $X^5$, $X^6$, $X^7$, $Y^3$, $Y^4$, $Y^5$, and $Y^6$ have independently of each other and preferably in any combinations of these variables preferably one of the following meanings:

A is NH;

$R^1$ is independently of its occurrence selected from the group consisting of halogen, CN, $C_1$-$C_4$-alkyl, fluorinated $C_1$-$C_4$-alkyl, $C_1$-$C_4$-alkoxy and $NR^aR^b$, in particular selected from halogen, $C_1$-$C_4$-alkyl and fluorinated $C_1$-$C_4$-alkyl, especially selected from halogen, methyl and trifluoromethyl;

$R^2$ is independently of its occurrence selected from the group consisting of halogen, CN, $C_1$-$C_6$-alkyl, halogenated (especially fluorinated) $C_1$-$C_6$-alkyl and $NR^aR^b$, in particular halogen;

$R^3$ is halogen;

m 0 or 1;

n 0 or 1;

o 0 or 1;

$R^4$ is hydrogen;

$X^1$ is N;

$X^2$ is CH or C—$R^2$, in particular CH;

$X^3$ is CH or C—$R^2$, in particular CH;

$X^4$ is CH or C—$R^1$, in particular CH;

$X^5$ is CH or C—$R^1$, in particular C—R';

$X^6$ is CH or C—$R^1$, in particular CH;

$X^7$ is CH or C—$R^1$, in particular CH;

$Y^3$ is CH or C—$R^3$, in particular CH;

$Y^4$ is N;

$Y^5$ is CH or C—$R^3$, in particular CH;

$Y^6$ is CH or C—$R^3$, in particular CH.

If present $R^a$ and $R^b$ are selected, independently of each other, from hydrogen or $C_1$-$C_4$-alkyl or $NR^aR^b$ forms a saturated 5- or 6-membered heterocycle, selected from piperidin-1-yl, piperazin-1-yl, morpholin-4-yl and pyrrolidin-1-yl.

The invention relates in particular to the compounds of the following embodiments 1A, 1B and 1C, i.e. to the compounds of the following formulae 1A, 1B and 1C, and to the stereoisomers, prodrugs and/or physiologically tolerated acid addition salts thereof, wherein A, $R^1$, $R^2$, $R^3$, $R^4$, $X^1$, $X^2$, $X^3$, $X^4$, $X^5$, $X^6$, $X^7$, $Y^3$, $Y^4$, $Y^5$, and $Y^6$ have the same meaning as defined herein or in any one of claims 1 to 15 and wherein m is 0 or 1, n is 0 or 1 and o is 0 or 1.

Preferred embodiment 1A (the symbols "A" and "B" in the bicyclic ring as well as the symbol "C" in the monocyclic ring of formula (I) are only part of the numbering system and represents no chemical meaning by themselves):

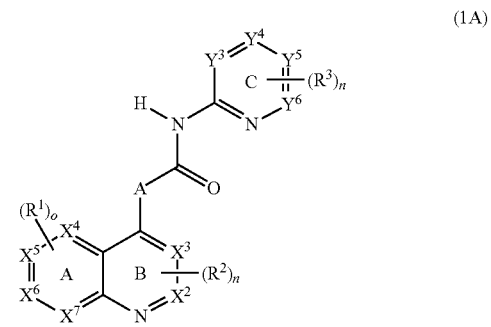

(1A)

In the embodiment 1A, A is preferably NH.

Preferred embodiment 1B (the symbol "C" in the monocyclic ring of formula (I) are only part of the numbering system and represents no chemical meaning by themselves):

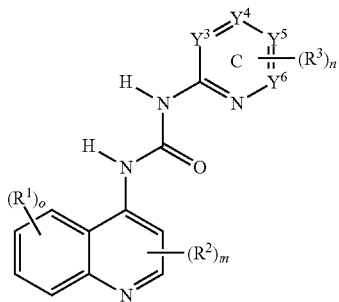

(1B)

Preferred embodiment 1C (the symbol "C" in the monocyclic ring of formula (I) is only part of the numbering system and represents no chemical meaning by themselves):

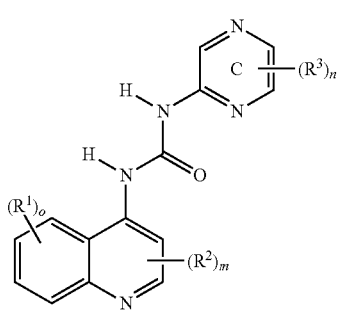

(1C)

Particularly preferred examples of compounds of the invention include

1-Pyrazin-2-yl-3-(6-trifluoromethyl-quinolin-4-yl)-urea;
1-Pyrazin-2-yl-3-(7-trifluoromethyl-quinolin-4-yl)-urea;
1-Pyrazin-2-yl-3-(8-trifluoromethyl-quinolin-4-yl)-urea;
1-(2-Methyl-quinolin-4-yl)-3-pyrazin-2-yl-urea;
1-Pyrazin-2-yl-3-quinolin-4-yl-urea;
1-Pyrazin-2-yl-3-(2-trifluoromethyl-quinolin-4-yl)-urea;
1-(6-Bromo-quinolin-4-yl)-3-pyrazin-2-yl-urea;
1-Pyridin-3-yl-3-quinolin-4-yl-urea;
1-Pyridin-3-yl-3-(7-trifluoromethyl-quinolin-4-yl)-urea;
1-Methyl-1-pyrazin-2-yl-3-(6-trifluoromethyl-quinolin-4-yl)-urea;
1-Isoquinolin-1-yl-3-pyrazin-2-yl-urea;
1-Pyrazin-2-yl-3-quinolin-8-yl-urea;
1-Isoquinolin-8-yl-3-pyrazin-2-yl-urea;
1-Pyrazin-2-yl-3-quinolin-5-yl-urea;
1-Isoquinolin-5-yl-3-pyrazin-2-yl-urea;
1-Isoquinolin-4-yl-3-pyrazin-2-yl-urea;

and the physiologically tolerated acid addition salts thereof.

Particularly preferred examples of compounds of the invention also include

1-Pyrazin-2-yl-3-(1,2,3,4-tetrahydro-acridin-9-yl)-urea;
1-Naphthalen-1-yl-3-pyrazin-2-yl-urea;
Pyrazine-2-carboxylic acid quinolin-4-ylamide;
Pyrazine-2-carboxylic acid (2-methyl-quinolin-4-yl)-amide;
Pyrazine-2-carboxylic acid isoquinolin-1-ylamide;

and the physiologically tolerated acid addition salts thereof.

Particularly preferred examples of compounds of the invention also include 1-(Pyrazin-2-yl)-3-(pyridin-4-yl)urea
1-(Quinolin-4-yl)-3-(pyrazin-2-yl)urea
1-(8-Fluoroquinolin-4-yl)-3-(pyrazin-2-yl)urea
1-(7-Iodoquinolin-4-yl)-3-(pyrazin-2-yl)urea
1-(7-Bromoquinolin-4-yl)-3-(pyrazin-2-yl)urea
1-(Pyridin-2-yl)-3-(7-(trifluoromethyl)quinolin-4-yl)urea
1-(8-Methylquinolin-4-yl)-3-(pyrazin-2-yl)urea
1-(8-Chloroquinolin-4-yl)-3-(pyrazin-2-yl)urea
1-(6-Morpholinopyridin-2-yl)-3-(8-(trifluoromethyl)quinolin-4-yl)urea
1-(8-Iodoquinolin-4-yl)-3-(pyrazin-2-yl)urea
1-(3-Bromoquinolin-4-yl)-3-(pyrazin-2-yl)urea
1-(6,8-Difluoroquinolin-4-yl)-3-(pyrazin-2-yl)urea
1-(8-Bromoquinolin-4-yl)-3-(pyrazin-2-yl)urea
1-(1,5-Naphthyridin-4-yl)-3-(pyrazin-2-yl)urea
1-(5-Chloro-1H-1,2,3-triazol-4-yl)-3-(7-(trifluoromethyl)quinolin-4-yl)urea and the physiologically tolerated acid addition salts thereof.

The compounds of the present invention can be prepared by analogy to routine techniques, a skilled person is familiar with. In particular, the compounds of the formula I can be prepared according to the following schemes, wherein $R^1$, $R^2$, $R^3$, $R^4$, m, n, o, $X^2$, $X^3$, $X^4$, $X^5$, $X^6$, $X^7$, $Y^3$, $Y^4$ and $Y^5$ are as defined above:

Scheme 1:

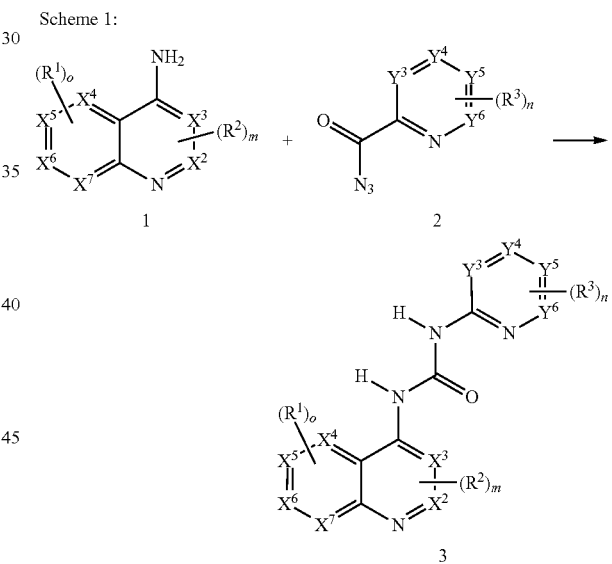

The amine 1 can be acylated by reaction with an acyl azide 2 (prepared by reaction of the corresponding acyl halide with a metal azide salt according to standard methods of organic chemistry) to give disubstituted ureas of general formula 3. The reaction is carried out in the presence of a suitable solvent such as toluene or N,N-dimethylformamide. The reaction is usually carried out at temperatures of from 20-120° C. Other conditions for describing this transformation (known as the Curtius rearrangement) are described in the following articles: Journal of Organic Chemistry, 1986, 51, 3007 & 5123; Journal of Organic Chemistry, 1987, 52, 4875; Tetrahedron Letters, 1984, 25, 3515; and Organic Reactions, 1947, 3, 337.

Disubstituted urea compounds of the general formula I can also be prepared according to a route depicted in scheme 2.

Scheme 2:

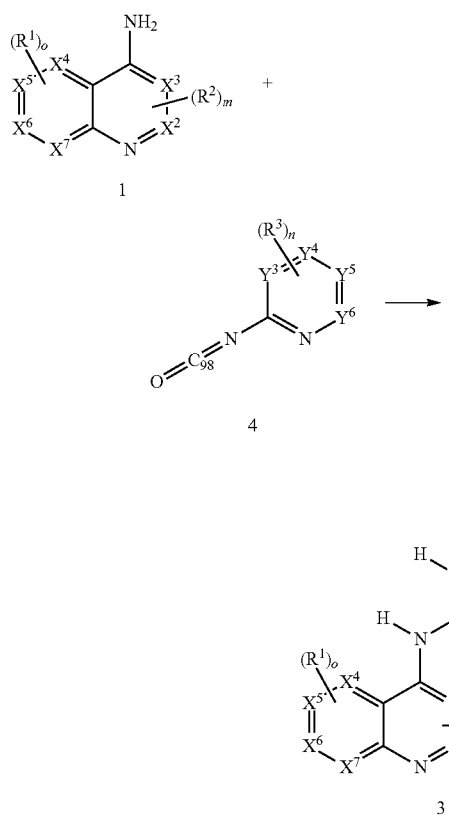

The amine 1 can be acylated by reaction with an isocyanate 4 to give disubstituted ureas of general formula 3. The reaction is carried out in the presence of a suitable solvent such as toluene or N,N-dimethylformamide. The reaction is usually carried out at temperatures of from 20-120° C.

Disubstituted urea compounds of the general formula I can also be prepared according to a route depicted in scheme 3.

Scheme 3:

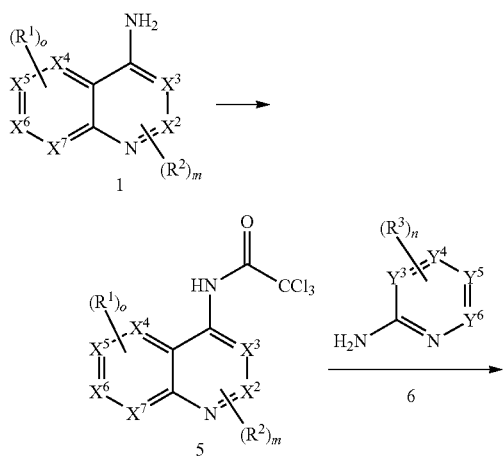

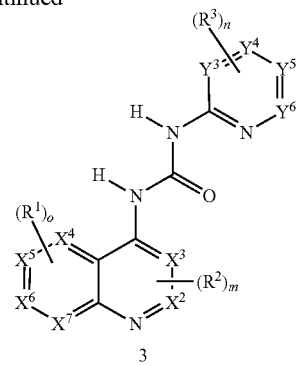

The amine 1 can be converted to trichloroacetamide 5 by reaction with trichloroacetyl chloride The reaction is carried out in the presence of a suitable solvent such as toluene or N,N-dimethylformamide. The reaction is usually carried out at temperatures of from 20-120° C. The trichloroacetamide 5 can be reacted with an amine 6 to give disubstituted ureas of general formula 3.

Amide analogs of the general formula 8 can also be prepared according to a route depicted in scheme 4.

Scheme 4:

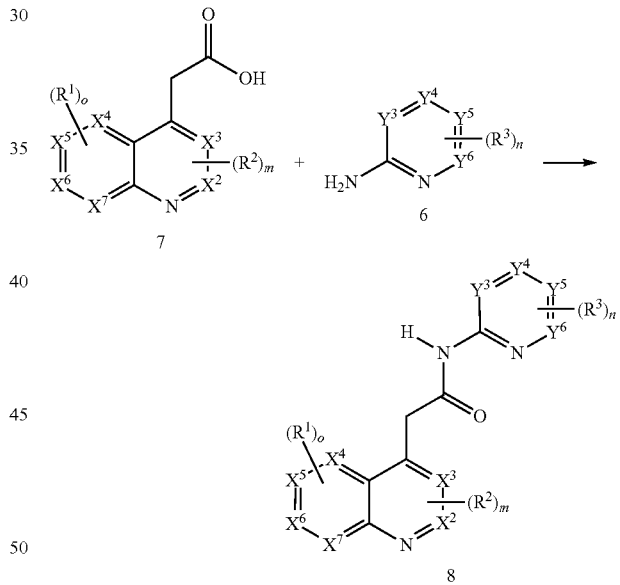

The carboxylic acid 7 can be converted to amide 8 by reaction an amine 6 using standard amide formation conditions familiar to those skilled in the art. The reaction is carried out in the presence of a suitable solvent such dimethylacetamide, N,N-dimethylformamide or THF. The reaction is usually carried out at temperatures of from 20-120° C. Coupling reagents such as HOBT or carbonyl diimidazole are employed.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", AndréLoupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of the formula I according to the present invention (and likewise the compounds of the formulae 1a, 1b and 1c), as well as the stereoisomers, the prodrugs and physiologically tolerated acid addition salts thereof, are capable of modulating the activity on glycogen synthase kinase 3β. In particular, the compounds of the formula I (and likewise the compounds of the formulae 1a, 1b and 1c), as well as the stereoisomers, the prodrugs and physiologically tolerated acid addition salts thereof, have an inhibitory activity on glycogen synthase kinase 3β. Amongst the compounds of the formula I those are preferred, which achieve effective inhibition at low concentrations. In particular, compounds of the formula I are preferred, which inhibit glycogen synthase kinase 3β at a level of $IC_{50}<1$ µMol, more preferably at a level of $IC_{50}<0.5$ µMol, particularly preferably at a level of $IC_{50}<0.2$ µMol and most preferably at a level of $IC_{50}<0.1$ µMol.

Therefore the compounds of the formula I according to the present invention, their prodrugs and their physiologically tolerated acid addition salts are useful for the treatment of a medical disorder susceptible to treatment with a compound that modulates glycogen synthase kinase 3β activity. As mentioned above, diseases caused by abnormal GSK-3β activity and which thus can be treated by supplying the compound of the formula I and/or an acid addition salt thereof, include in particular neurodegenerative diseases such as Alzheimer's disease. In addition, the compounds of the present invention are also useful for treatment of other neurodegenerative diseases such as Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Within the context of the treatment, the use according to the invention of the compounds of the formula I involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semi-solid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; anti irritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the invention without limiting it.

The compounds were either characterized via proton-NMR in $d_6$-dimethylsulfoxide or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

Preparation Examples 1, 2, 5, 6, 7, 8, 9, 10, 12, 14, 15, 17, 19, 20, 21, 22, 23, and 24 to 40

Example 1

1-Pyrazin-2-yl-3-(2-trifluoromethyl-quinolin-4-yl)-urea

A solution of 300 mg (1.41 mmol) of 4-amino-2-trifluoromethylquinoline and 235 mg (1.56 mmol) of pyrazine-2-carbonyl azide in 20 ml of toluene was stirred at 80° C. for 18 h. The solution was allowed to cooled to RT and stirred for a further 16 h. The resulting solid precipitate was collected by filtration, washed with toluene and dried in a vacuum oven at 40° C. White solid. Amount 320 mg. Yield 67.9%.
$^1$H-NMR (DMSO-$d_6$, 400 MHz) δ 7.90 (m, 2H), 8.14 (d, 1H), 8.33 (m, 2H), 8.47 (s, 1H), 8.72 (s, 1H), 9.13 (m, 2H), 10.26 (br s, 1H); MS (APCI+) m/z 334.0 (M+H$^+$, 100%).

Example 2

1-(6-Bromo-quinolin-4-yl)-3-pyrazin-2-yl-urea

Prepared by the method described for Example 1. White solid. Amount 415 mg. Yield 89.7%.
$^1$H-NMR (DMSO-$d_6$, 400 MHz) δ 7.92 (q, 2H), 8.30 (d, 1H), 8.37 (m, 2H), 8.47 (s, 1H), 8.71 (d, 1H), 9.19 (s, 1H), 10.09 (br s, 2H); MS (APCI+) m/z 344.0, 346.0 (M+H$^+$, 100%).

Example 5

1-Pyrazin-2-yl-3-(1,2,3,4-tetrahydro-acridin-9-yl)-urea

Prepared by the method described for Example 1. White solid. Amount 92 mg. Yield 45.1%.
$^1$H-NMR (DMSO-$d_6$, 400 MHz) δ 1.81 (m, 2H), 1.90 (m, 2H), 2.86 (t, 2H), 3.05 (m, 2H), 7.50 (t, 1H), 7.65 (t, 1H), 7.90 (t, 2H), 8.92 (s, 1H), 9.19 (s, 2H), 10.26 (br s, 2H); MS (APCI+) m/z 320.0 (M+H$^+$, 100%).

Example 6

1-Isoquinolin-4-yl-3-pyrazin-2-yl-urea

Prepared by the method described for Example 1. White solid. Amount 242 mg. Yield 87.7%.
$^1$H-NMR (DMSO-$d_6$, 400 MHz) δ 7.50 (t, 1H), 7.65 (t, 1H), 8.14 (dd, 2H), 8.30 (s, 1H), 8.40 (s, 1H), 9.04 (s, 1H), 9.08 (s, 1H), 9.11 (s, 1H), 10.09 (br s, 2H); MS (APCI+) m/z 266.0 (M+H$^+$, 100%).

Example 7

1-Naphthalen-1-yl-3-pyrazin-2-yl-urea

Prepared by the method described for Example 1. White solid. Amount 781 mg. Yield 84.6%.
$^1$H-NMR (DMSO-$d_6$, 400 MHz) δ 7.48-7.67 (m, 3H), 7.69 (d, 1H), 7.96 (d, 1H), 8.12 (dd, 2H), 8.30 (s, 1H), 8.39 (s, 1H), 9.02 (s, 1H), 10.00 (s, 1H), 10.08 (br s, 1H); MS (APCI+) m/z 265.1 (M+H$^+$, 100%).

Example 8

1-Pyrazin-2-yl-3-(8-trifluoromethyl-quinolin-4-yl)-urea

Prepared by the method described for Example 1. White solid. Amount 141 mg. Yield 44.8%.
$^1$H-NMR (DMSO-$d_6$, 400 MHz) rotamers δ 7.83 (t, 1H), 8.22 (d, 1H), 8.30-8.55 (m, 3H), 8.51 (d, 1H), 8.90 (d, 1H), 9.11 (s, 1H), 9.14 (s, 1H), 10.24 (br s, 2H); MS (APCI+) m/z 334.1 (M+H$^+$, 100%).

Example 9

1-Pyrazin-2-yl-3-(7-trifluoromethyl-quinolin-4-yl)-urea

Prepared by the method described for Example 1. White solid. Amount 660 mg. Yield 84.1%.
$^1$H-NMR (DMSO-$d_6$, 400 MHz) δ 8.02 (d, 1H), 8.34 (d, 2H), 8.38-8.49 (m, 3H), 8.90 (d, 1H), 9.09 (s, 1H), 10.24 (s, 1H), 10.57 (br s, 1H); MS (APCI+) m/z 334.0 (M+H$^+$, 100%).

Example 10

1-Pyrazin-2-yl-3-quinolin-4-yl-urea

Example 10 was prepared by the method described for Example 1. White solid. Amount 386 mg. Yield 69.9%.
$^1$H-NMR (DMSO-$d_6$, 400 MHz) δ 7.72 (t, 1H), 7.80 (t, 1H), 8.00 (d, 1H), 8.21 (d, 3H), 8.27 (d, 1H), 8.34 (s, 1H), 8.45 (s, 1H), 8.78 (d, 1H), 9.08 (s, 1H), 10.24 (5, 1H), 10.44 (br s, 1H); MS (APCI+) m/z 266.1 (M+H$^+$, 100%).

Example 12

1-(2-Methyl-quinolin-4-yl)-3-pyrazin-2-yl-urea

Example 12 was prepared by the method described for Example 1. White solid. Amount 708 mg. Yield 81.8%.
$^1$H-NMR (DMSO-$d_6$, 400 MHz) δ 2.62 (s, 3H), 7.52 (m, 1H), 7.74 (m, 1H), 7.88 (d, 1H), 8.15 (m, 3H), 8.32 (s, 2H), 8.42 (d, 1H), 9.09 (s, 1H), 10.24 (s, 1H), 10.39 (br s, 1H); MS (APCI+) m/z 280.1 (M+H$^+$, 100%).

Example 14

1-Pyrazin-2-yl-3-(6-trifluoromethyl-quinolin-4-yl)-urea

Prepared by the method described for Example 1. White solid. Amount 657 mg. Yield 83.7%.
$^1$H-NMR (DMSO-$d_6$, 400 MHz) δ 8.03 (d, 1H), 8.19 (d, 1H), 8.38 (m, 3H), 8.67 (s, 1H), 8.91 (d, 1H), 9.17 (s, 1H), 10.28 (br s, 1H); MS (APCI+) m/z 334.0 (M+H$^+$, 100%).

Example 15

1-Isoquinolin-1-yl-3-pyrazin-2-yl-urea

Example 15 was prepared by the method described for Example 1. White solid. Amount 676 mg. Yield 73.5%. (159 mg amide)

$^1$H-NMR (DMSO-$d_6$, 400 MHz) δ 2.62 (s, 3H), 7.52 (m, 1H), 7.74 (m, 1H), 7.88 (d, 1H), 8.15 (m, 3H), 8.32 (s, 2H), 8.42 (d, 1H), 9.09 (s, 1H), 10.24 (s, 1H), 10.39 (br s, 1H); MS (APCI+) m/z 280.1 (M+H$^+$, 100%).

Example 17

1-Pyrazin-2-yl-3-quinolin-8-yl-urea

Prepared by the method described for Example 1. White solid. Amount 828 mg. Yield 90.0%.

$^1$H-NMR (DMSO-$d_6$, 400 MHz) δ 7.61 (m, 3H), 8.28 (5, 1H), 8.38 (5, 1H), 8.40 (5, 1H), 8.61 (d, 1H), 8.97 (m, 1H), 9.06 (5, 1H), 10.45 (5, 1H), 11.18 (br s, 1H); MS (APCI+) m/z 266.1 (M+H$^+$, 100%).

Example 19

1-Isoquinolin-8-yl-3-pyrazin-2-yl-urea

Prepared by the method described for Example 1. White solid. Amount 815 mg. Yield 88.6%.

$^1$H-NMR (DMSO-$d_6$, 400 MHz) δ 7.72 (m, 2H), 7.86 (d, 1H), 8.20 (d, 1H), 8.30 (s, 1H), 8.57 (d, 1H), 9.09 (s, 1H), 9.56 (s, 1H), 10.00 (br s, 1H), 10.24 (br s, 1H); MS (APCI+) m/z 266.2 (M+H$^+$, 100%).

Example 20

1-Isoquinolin-5-yl-3-pyrazin-2-yl-urea

Prepared by the method described for Example 1. White solid. Amount 470 mg. Yield 85.1%.

$^1$H-NMR (DMSO-$d_6$, 400 MHz) δ 7.69 (t, 1H), 7.88 (d, 1H), 7.98 (d, 1H), 8.30 (s, 1H), 8.37 (d, 1H), 8.41 (s, 1H), 8.63 (d, 1H), 9.05 (s, 1H), 9.34 (s, 1H), 10.60 (br s, 1H), 10.17 (br s, 1H); MS (APCI+) m/z 266.2 (M+H$^+$, 100%).

Example 21

1-Pyrazin-2-yl-3-quinolin-5-yl-urea

Prepared by the method described for Example 1. White solid. Amount 510 mg. Yield 92.4%.

$^1$H-NMR (DMSO-$d_6$, 400 MHz) δ 7.63 (m, 1H), 7.78 (m, 2H), 8.13 (d, 1H), 8.30 (d, 1H), 8.40 (s, 1H), 8.54 (d, 1H), 8.94 (s, 1H), 9.06 (s, 1H), 9.98 (br s, 1H), 10.12 (br s, 1H); MS (APCI+) m/z 266.2 (M+H$^+$, 100%).

Example 22

1-Methyl-1-pyrazin-2-yl-3-(6-trifluoromethyl-quinolin-4-yl)-urea

A solution of 145 mg (0.44 mmol) of 1-pyrazin-2-yl-3-(6-trifluoromethyl-quinolin-4-yl)-urea (Example 14) and 16 mg (0.65 mmol) of sodium hydride in 10 ml of dimethylformamide was stirred at 0° C. for 10 min. Methyl iodide (93 mg, 0.65 mmol) was added and the solution was allowed to reach RT and stirred for a further 16 h. The solution was concentrated in vacuo, and partitioned between dichloromethane and water. The organic layer was washed 3 times with water, concentrated in vacuo and the material purified by chromatography. White solid. Amount 32 mg. Yield 21.2%.

$^1$H-NMR (CDCl$_3$, 400 MHz) δ 3.67 (s, 3H), 7.60 (s, 1H), 7.91 (d, 1H), 8.17 (d, 2H), 8.47 (m, 4H), 8.73 (s, 1H), 8.84 (d, 1H); MS (APCI+) m/z 338.0 (M+H$^+$, 100%).

Example 23

N-Pyrazin-2-yl-2-quinolin-4-yl-acetamide

A solution of 200 mg (0.89 mmol) of quinolin-4-yl-acetic acid hydrochloride salt and 145 mg (0.89 mmol) of N,N-carboyl diimidazole was stirred in 3 ml of dimethylformamide at RT for 2 h. 2-Aminopyrazine (63 mg, 0.66 mmol) in 2 ml of pyridine was added dropwise over 10 mins and stirred at 80° C. for a further 9 h. The solution was allowed to cool, concentrated in vacuo, and partitioned between dichloromethane and water. The organic layer was washed 3 times with water, concentrated in vacuo and the material purified by chromatography. White solid. Amount 108 mg. Yield 62%.

MS (APCI+) m/z 265.1 (M+H$^+$, 100%).

Example 24

1-(Pyrazin-2-yl)-3-(pyridin-4-yl)urea

Prepared by the method described for Example 1. White solid. Amount 573 mg. Yield 84%.

$^1$H-NMR (DMSO-$d_6$, 400 MHz) δ 7.98 (m, 1H), 8.23 (m, 1H), 8.42 (m, 4H), 9.13 (s, 1H), 10.18 (s, 1H), 10.26 (br s, 1H), 10.52 (br s, 1H); MS (APCI+) m/z 267.1 (M+H$^+$, 100%).

Example 25

1-(Quinolin-4-yl)-3-(pyrazin-2-yl)urea

Prepared by the method described for Example 1. White solid. Amount 210 mg. Yield 57%.

$^1$H-NMR (DMSO-$d_6$, 400 MHz) δ 7.63 (m, 1H), 7.78 (m, 2H), 8.13 (d, 1H), 8.30 (d, 1H), 8.40 (s, 1H), 8.54 (d, 1H), 8.94 (s, 1H), 9.06 (s, 1H), 9.98 (br s, 1H), 10.12 (br s, 1H); MS (APCI+) m/z 266.2 (M+H$^+$, 100%).

Example 26

1-(8-Fluoroquinolin-4-yl)-3-(pyrazin-2-yl)urea

Prepared by the method described for Example 1. White solid. Amount 310 mg. Yield 92%.

$^1$H-NMR (DMSO-$d_6$, 400 MHz) δ 7.67 (m, 2H), 8.02 (d, 1H), 8.34 (m, 2H), 8.48 (s, 1H), 8.82 (d, 1H), 9.07 (s, 1H), 9.12 (s, 1H), 10.26 (br s, 1H), 10.49 (br s, 1H); MS (APCI+) m/z 284.0 (M+H$^+$, 100%).

Example 27

1-(7-Iodoquinolin-4-yl)-3-(pyrazin-2-yl)urea

Prepared by the method described for Example 1. Yellow solid. Amount 112 mg. Yield 77%.

¹H-NMR (DMSO-d₆, 400 MHz) δ 7.88 (s, 2H), 8.27 (d, 1H), 8.36 (s, 1H), 8.45 (s, 1H), 8.76 (d, 1H), 9.09 (s, 1H), 10.19 (br s, 1H), 10.42 (br s, 1H); MS (APCI+) m/z 392.0 (M+H⁺, 100%).

Example 28

1-(7-Bromoquinolin-4-yl)-3-(pyrazin-2-yl)urea

Prepared by the method described for Example 1. Yellow solid. Amount 125 mg. Yield 81%.
¹H-NMR (DMSO-d₆, 400 MHz) δ 7.18 (m, 1H), 7.22 (m, 1H), 7.63 (t, 1H), 8.22 (d, 1H), 8.27 (d, 1H), 8.36 (s, 1H), 8.46 (s, 1H), 8.78 (d, 1H), 9.09 (s, 1H), 10.19 (br s, 1H), 10.42 (br s, 1H);
MS (APCI+) m/z 266.2 (M+H⁺, 100%).

Example 29

1-(Pyridin-2-yl)-3-(7-(trifluoromethyl)quinolin-4-yl)urea

Prepared by the method described for Example 1 using pyridin-2-carbonylazide. White solid. Amount 30 mg. Yield 10%.
¹H-NMR (DMSO-d₆, 400 MHz) δ 7.16 (t, 1H), 7.48 (m, 1H), 7.86 (t, 1H), 8.08 (d, 1H), 8.32 (s, 1H), 8.44 (m, 2H), 8.50 (d, 1H), 8.90 (d, 1H), 10.18 (br s, 1H);
MS (APCI+) m/z 333.1 (M+H⁺, 100%).

Example 30 (Comparative)

1-Phenyl-3-(quinolin-4-yl)urea

Prepared by the method described for Example 1 using phenylisocyanate. White solid. Amount 345 mg. Yield 76%.
¹H-NMR (DMSO-d₆, 400 MHz) δ 7.05 (t, 1H), 7.38 (m, 2H), 7.66 (m, 1H), 7.75 (m, 1H), 7.98 (d, 1H), 8.20 (d, 1H), 8.72 (d, 1H), 9.25 (br s, 2H);
MS (APCI+) m/z 265.0 (M+H⁺, 100%).

Example 31

1-(8-Methylquinolin-4-yl)-3-(Pyrazin-2-yl)urea

Prepared by the method described for Example 1. White solid. Amount 202 mg. Yield 76%.
¹H-NMR (DMSO-d₆, 400 MHz) δ 7.60 (t, 1H), 7.66 (m, 1H), 8.07 (d, 1H), 8.28 (d, 1H), 8.34 (s, 1H), 8.43 (s, 1H), 8.78 (d, 1H), 9.08 (s, 1H), 10.30 (br s, 2H);
MS (APCI+) m/z 280.0 (M+H⁺, 100%).

Example 32

1-(8-Chloroquinolin-4-yl)-3-(pyrazin-2-yl)urea

Prepared by the method described for Example 1. White solid. Amount 200 mg. Yield 79%.
¹H-NMR (DMSO-d₆, 400 MHz) δ 7.70 (t, 2H), 8.00 (d, 1H), 8.20 (d, 1H), 8.34 (m, 2H), 8.46 (s, 1H), 8.88 (d, 1H), 9.07 (s, 1H), 10.22 (br s, 1H), 10.50 (br s, 1H);
MS (APCI+) m/z 300.0 (M+H⁺, 100%).

Example 33

1-(6-Morpholinopyridin-2-yl)-3-(8-(trifluoromethyl)quinolin-4-yl)urea

Prepared by the method described for Example 1 using 4-(6-isocyanatopyridin-2-yl)morpholine. White solid. Amount 97 mg. Yield 20%.
¹H-NMR (DMSO-d₆, 400 MHz) δ 3.72 (s, 4H), 3.48 (s, 4H), 6.50 (d, 1H), 7.20 (d, 1H), 7.62 (t, 1H), 7.70 (t, 1H), 8.20 (d, 1H), 8.37 (d, 1H), 8.55 (d, 1H), 8.87 (d, 1H), 9.62 (s, 1H), 10.13 (br s, 1H);
MS (APCI+) m/z 418.1 (M+H⁺, 100%).

Example 34

1-(8-Iodoquinolin-4-yl)-3-(pyrazin-2-yl)urea

Prepared by the method described for Example 1. Yellow solid. Amount 1.25 g. Yield 43%.
¹H-NMR (DMSO-d₆, 400 MHz) δ 7.46 (t, 2H), 8.24 (d, 1H), 8.34 (m, 2H), 8.42 (m, 2H), 8.83 (d, 1H), 9.10 (s, 1H), 10.30 (br s, 2H);
MS (APCI+) m/z 391.9 (M+H⁺, 100%).

Example 35

1-(3-Bromoquinolin-4-yl)-3-(pyrazin-2-yl)urea 1-(Pyrazin-2-yl)-3-(quinolin-4-yl)urea (220 mg, 0.754 mmol) was dissolved in acetonitrile (3 mL) and N-bromosuccinamide was added (201 mg, 1.13 mmol). The resulting solution was heated at 80 C under microwave irradiation for 35 mins. The cooled solution was then partitioned between NaHCO3 solution and dichloromethane. The organic layer was separated, dried (MgSO4), filtered and concentrated to give the product. Yellow solid. Amount 204 mg. Yield 79%.
¹H-NMR (DMSO-d₆, 400 MHz) δ 7.68 (t, 1H), 7.81 (t, 1H), 8.05 (m, 2H), 8.27 (s, 1H), 8.33 (s, 1H), 9.01 (m, 2H), 10.00 (br s, 2H);
MS (APCI+) m/z 344.0, 346.0 (M+H⁺, 100%).

Example 36

1-(6,8-Difluoroquinolin-4-yl)-3-(Pyrazin-2-yl)urea

Prepared by the method described for Example 1. White solid. Amount 201 mg. Yield 80%.
¹H-NMR (DMSO-d₆, 400 MHz) δ 7.80 (m, 2H), 8.36 (m, 4H), 8.80 (d, 1H), 9.16 (s, 1H), 9.98 (s, 1H), 10.10 (br s, 1H);
MS (APCI+) m/z 302.0 (M+H⁺, 100%).

Example 37

1-(8-Bromoquinolin-4-yl)-3-(pyrazin-2-yl)urea

Prepared by the method described for Example 1. Yellow solid. Amount 145 mg. Yield 94%.
¹H-NMR (DMSO-d₆, 400 MHz) δ 7.18 (m, 1H), 7.22 (m, 1H), 7.63 (t, 1H), 8.22 (d, 1H), 8.27 (d, 1H), 8.35 (m, 2H), 8.46 (s, 1H), 8.88 (d, 1H), 9.09 (s, 1H), 10.2-10.5 (br d, 2H);
MS (APCI+) m/z 266.2 (M+H⁺, 100%).

Example 38

1-(1,5-Naphthyridin-4-yl)-3-(pyrazin-2-yl)urea

Prepared by the method described for Example 1. Yellow solid. Amount 320 mg. Yield 87%.
$^1$H-NMR (DMSO-$d_6$, 400 MHz) δ 7.88 (m, 1H), 8.43 (d, 1H), 8.42 (s, 1H), 8.50 (d, 1H), 8.84 (d, 1H), 9.11 (m, 1H), 10.32 (s, 1H), 10.65 (s, 1H), 11.40 (br s, 1H); MS (APCI+) m/z 266.3 (M+H$^+$, 100%).

Example 39

1-(5-Chloro-1H-1,2,3-triazol-4-yl)-3-(7-(trifluoromethyl)quinolin-4-yl)urea

Prepared by the method described for Example 1 using 4-chloro-1H-1,2,3-triazole-5-carbonyl azide and 7-(trifluoromethyl)quinolin-4-amine.
MS (APCI+) m/z 357.1 (M+H$^+$, 100%).

Example 40 (Comparative)

1-(Pyrazin-2-yl)-3-(quinolin-3-yl)urea

Prepared by the method described for Example 1. White solid. Amount 392 mg. Yield 85%.
$^1$H-NMR (DMSO-$d_6$, 400 MHz) δ 7.60 (m, 2H), 7.93 (m, 2H), 8.30 (s, 1H), 8.36 (s, 1H), 8.60 (s, 1H), 8.87 (s, 1H), 9.08 (s, 1H), 9.77 (br s, 1H), 10.08 (br s, 1H);
MS (APCI+) m/z 266.1 (M+H$^+$, 100%).

Biological Tests:

The compounds according to the invention exhibit very good affinities for GSK-3 (<1 μM, frequently<100 nM) and exhibited good selectivity against multiple kinase targets.

Methods—Biochemical hGSK-3Beta Assay

Compounds were tested for their ability to inhibit human Glycogen Synthase Kinase-3 beta (hGSK-3β) to phosphorylate biotin-YRRAAVPPSPSLSRHSSPHQ(pS)EDEEE. Compounds were incubated with 0.5 μCi 33P-ATP, 10 μM ATP, 0.0125 U hGSK-3β (Upstate cell signaling solutions) and 1 μM substrate (biotin-YRRAAVPPSPSLSRHSSPHQ (pS)EDEEE) in 50 mM HEPES, 10 mM MgCl$_2$, 100 mM Na$_3$VO$_4$, 1 mM DTT, 0.0075% Triton, 2% DMSO (total volume 50 μL) for 30 minutes at room temperature. The incubation was stopped by addition of an equal volume of 100 mM EDTA, 4M NaCl. 80 μL of this mixture was added to streptavidin-coated Flashplates (PerkinElmer). Following a wash step, 33P incorporation was quantified on a MicroBeta microplate liquid scintillation counter (Perkin Elmer). IC$_{50}$'s were determined by fitting a sigmoidal dose-response curve to the counts obtained at the different concentrations in Graph Pad Prism.

Methods—β-Catenin Reporter-Gene Assay

Compounds were tested for their ability to modulate β-catenin-modulated gene transcription in a LEF/TCF(T-cell factor) reporter gene assay. SY-SY5Y human neuroblastoma cells were transiently transfected with 80 ng/well TOPFLASH plasmid (Upstate cell signaling solutions) containing two sets of three copies of the TCF binding site upstream of the Thymidine Kinase minimal promoter and firefly Luciferase open reading frame or with 80 ng/well FOPFLASH plasmid (Upstate cell signaling solutions) containing three copies of a mutated TCF binding site upstream of the Thymidine Kinase minimal promoter and firefly Luciferase open reading frame. In addition all cells were transiently transfected with the 20 ng/well pRL-TK plasmid (Promega) containing the herpes simplex virus thymidine kinase promoter to provide low to moderate levels of *Renilla* Luciferase expression. Transfection medium was exchanged for serum-free medium containing the test substance and incubated for 24 h at 37 degree C. The incubation was stopped and quantified using the Dual Glo Luciferase Assay (Promega) as indicated and quantified on a Pherastar reader (BMG).

Firefly Luciferase activity was normalised for *Renilla* Luciferase activity per well. Subsequently, the normalised TOPFLASH response was compared to the normalised FOPFLASH response, thus giving the LEF/TCF specific signal. The maximal response is the maximal ratio between the normalised TOPFLASH and FOPFLASH signals. Sigmoidal dose-response curves were fitted using Graphpad Prism.

The results of the binding tests are given in the table below.

| Example # | GSK-3β IC$_{50}$ | Cellular Activity in GSK-3β TOPFLASH assay |
|---|---|---|
| 2 | +++ | ++ |
| 10 | +++ | +++ |
| 14 | +++ | +++ |
| 9 | +++ | +++ |
| 8 | +++ | +++ |
| 12 | ++ | n.d. |
| 21 | ++ | n.d. |
| 6 | ++ | n.d. |
| 20 | ++ | n.d. |
| 19 | ++ | n.d. |
| 1 | ++ | n.d. |
| 5 | ++ | n.d. |
| 7 | + | n.d. |
| 15 | + | n.d. |
| 16 | + | n.d. |
| 22 | + | n.d. |
| 26 | +++ | n.d. |
| 27 | +++ | n.d. |
| 28 | +++ | n.d. |
| 32 | +++ | n.d. |
| 36 | +++ | n.d. |
| 37 | +++ | n.d. |
| 33 | +++ | n.d. |
| 34 | +++ | n.d. |
| 31 | +++ | n.d. |
| 29 | ++ | n.d. |
| 25 | ++ | n.d. |
| 35 | ++ | n.d. |
| 24 | ++ | n.d. |
| 40* | + | n.d. |
| 30* | + | n.d. |
| 38 | n.d. | n.d. |
| 39 | n.d. | n.d. | n.d. not determined;
*Comparative Example
GSK-3β IC$_{50}$:
+ >10 μM
++ from 100 nM to 10 μM
+++ <100 nM

The invention claimed is:

1. A method for therapeutically treating a medical disorder selected from the group consisting of Alzheimer's disease, Parkinson's disease, a tauopathy, non-insulin dependent diabetes, obesity, manic depressive illness, schizophrenia, breast cancer, non-small cell lung carcinoma, thyroid cancer, T-cell leukemia, B-cell leukemia, and a virus-induced tumor, said method comprising administering to a subject in need thereof an effective amount of at least one compound of the formula (I)

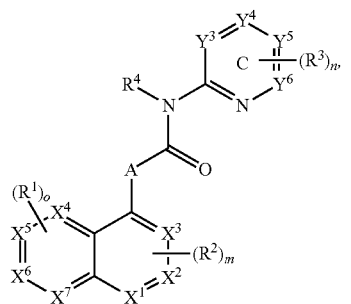

(I)

a stereoisomer, or physiologically tolerated acid addition salt thereof, wherein A is NH;
$X^1$ is N;
$X^2$ is selected from the group consisting of CH and $CR^2$;
$X^3$ is selected from the group consisting of CH and $CR^2$;
$X^4$, $X^5$, $X^6$, and $X^7$ are independently of each other selected from the group consisting of CH and $CR^1$;
$Y^3$, $Y^5$ and $Y^6$ are independently of each other selected from the group consisting of CH and $CR^3$;
$Y^4$ is selected from the group consisting of CH, $CR^3$, and N resulting in a 6-membered ring C;
n is the number of residues $R^3$ and is 0, 1, 2, 3, or 4;
m is the number of residues $R^2$ and is 0, 1, or 2;
o is the number of residues $R^1$ and is 0, 1, 2, 3, or 4;
$R^1$, $R^3$ are independently of each other and independently of each occurrence selected from the group consisting of $NH_2$, NH—$C_1$-$C_6$-alkyl, $NR^aR^b$, OH, =O, $C_1$-$C_6$-alkoxy, $C_1$-$C_6$-haloalkoxy, halogen, $C_1$-$C_4$-alkyl, $C_3$-$C_7$-cycloalkyl, $C_2$-$C_4$-alkenyl, halogenated $C_1$-$C_4$-alkyl, halogenated $C_3$-$C_7$-cycloalkyl, halogenated $C_2$-$C_4$-alkenyl, formyl, $C_1$-$C_6$-alkylcarbonyl, $C_1$-$C_6$-alkyl-$NR^aR^b$, and an aromatic radical Ar, which is selected from the group consisting of phenyl and a 5- or 6-membered N- or C-bound heteroaromatic radical, comprising 1 nitrogen atom as ring member and 0, 1, 2 or 3 further heteroatoms, independently selected from the group consisting of O, S and N, as ring members, wherein Ar is unsubstituted or carries one or two radicals $R^{1a}$;
$R^2$ is independently of its occurrence selected from the group consisting of halogen, CN, halogenated $C_1$-$C_6$-alkyl, $NR^aR^b$; or for m=2 or 3 two of $R^2$ at $X^2$ and $X^3$ can form together a fused 5- or 6-membered aliphatic cyclic ring which may contain 1 or 2 heteroatoms as ring members selected from the group consisting of N, O and S and which can be substituted with 1, 2 or 3 residues $R^3$ independently of each other having a meaning as defined above;
$R^{1a}$ is independently of each other and independently of its occurrence selected from the group consisting of halogen, $C_1$-$C_6$-alkyl, $C_3$-$C_6$-cycloalkyl, $C_1$-$C_6$-alkoxy, halogenated $C_1$-$C_6$-alkyl, halogenated $C_3$-$C_6$-cycloalkyl, halogenated $C_1$-$C_6$-alkoxy, $NR^aR^b$, 1-aziridinyl, azetidin-1-yl, pyrrolidin-1-yl, piperidin-1-yl, morpholin-4-yl, homopiperidin-1-yl, a phenyl group, and an aromatic 5- or 6-membered C-bound heteroaromatic radical comprising 1 nitrogen atom as ring member and 0, 1, 2, or 3 further heteroatoms independently selected from the group consisting of O, S, and N, as ring members, wherein phenyl and the heteroaromatic radical are, independently of each other, unsubstituted or substituted by 1, 2, 3, or 4 radicals selected from the group consisting of halogen, cyano, $C_1$-$C_4$-alkyl, halogenated $C_1$-$C_4$-alkyl, $C_1$-$C_4$-alkoxy, and halogenated $C_1$-$C_4$-alkoxy;
$R^a$, $R^b$ are independently selected from the group consisting of H, $C_1$-$C_4$-alkyl halogenated $C_1$-$C_4$-alkyl, and $C_1$-$C_4$-alkoxy; or $R^a$, $R^b$ may form, together with the nitrogen atom to which they are bound, a 4-, 5-, 6-, or 7-membered saturated or unsaturated N-heterocyclic ring, which may carry 1 further heteroatom selected from the group consisting of O, S, and N as a ring member; and
$R^4$ is selected from the group consisting of H, $C_1$-$C_4$-alkyl, and halogenated $C_1$-$C_6$-alkyl.

2. The method according to claim 1, wherein medical disorder is Alzheimer's disease.

3. The method according to claim 1, wherein
$Y^4$ is N;
$R^1$, $R^3$ are independently of each other and independently of each occurrence selected from the group consisting of $NH_2$, NH—$C_1$-$C_6$-alkyl, $NR^aR^b$, OH, =O, $C_1$-$C_6$-alkoxy, $C_1$-$C_6$-haloalkoxy, halogen, $C_1$-$C_4$-alkyl, $C_3$-$C_7$-cycloalkyl, $C_2$-$C_4$-alkenyl, fluorinated $C_1$-$C_6$-alkyl, fluorinated $C_3$-$C_7$-cycloalkyl, fluorinated $C_2$-$C_4$-alkenyl, formyl, $C_1$-$C_6$-alkylcarbonyl, $C_1$-$C_6$-alkyl-$NR^aR^b$, and an aromatic radical Ar, which is selected from the group consisting of phenyl and a 5- or 6-membered or C-bound heteroaromatic radical, comprising 1 nitrogen atom as ring member and 0, 1, 2, or 3 further heteroatoms, independently selected from the group consisting of O, S, and N, as ring members, wherein Ar is unsubstituted or carries one or two radicals $R^{1a}$;
$R^2$ is independently of its occurrence selected from the group consisting of halogen, CN, fluorinated $C_1$-$C_6$-alkyl, and $NR^aR^b$;
$R^{1a}$ is independently of each other and independently of its occurrence selected from the group consisting of halogen, $C_1$-$C_6$-alkyl, $C_3$-$C_6$-cycloalkyl, $C_1$-$C_6$-alkoxy, fluorinated $C_1$-$C_6$-alkyl, fluorinated $C_3$-$C_6$-cycloalkyl, fluorinated $C_1$-$C_6$-alkoxy, $NR^aR^b$, 1-aziridinyl, azetidin-1-yl, pyrrolidin-1-yl, piperidin-1-yl, morpholin-4-yl, homopiperidin-1-yl, a phenyl group, and an aromatic 5- or 6-membered C-bound heteroaromatic radical comprising 1 nitrogen atom as ring member and 0, 1, 2, or 3 further heteroatoms independently selected from the group consisting of O, S, and N, as ring members, wherein phenyl and the heteroaromatic radical are, independently of each other, unsubstituted or substituted by 1, 2, 3, or 4 radicals selected from the group consisting of halogen, cyano, $C_1$-$C_4$-alkyl, fluorinated $C_1$-$C_4$-alkyl, $C_1$-$C_4$-alkoxy, and fluorinated $C_1$-$C_4$-alkoxy; and
$R^a$, $R^b$ are independently selected from the group consisting of H, $C_1$-$C_4$-alkyl, fluorinated $C_1$-$C_4$-alkyl, and $C_1$-$C_4$-alkoxy; or $R^a$, $R^b$ may form, together with the nitrogen atom to which they are bound, a 4-, 5-, 6-, or 7-membered saturated or unsaturated N-heterocyclic ring, which may carry 1 further heteroatom selected from the group consisting of O, S, and N as a ring member.

4. The method according to claim 1, wherein $X^3$ is CH.
5. The method according to claim 1, wherein $Y^4$ is N.
6. The method according to claim 1, wherein $R^3$, if present, is halogen.

7. The method according to claim 1, wherein
m is 0 or 1; and
$R^2$ is halogen.

8. The method according to claim 1, wherein
o is 1; and
$R^1$ is selected from the group consisting of H, halogen, $C_1$-$C_4$-alkyl, and halogenated $C_1$-$C_4$-alkyl.

9. The method according to claim 1, wherein
$R^1$ at least is located at $X^5$ and independently of its occurrence is selected from the group consisting of halogen, $C_1$-$C_4$-alkyl, and halogenated $C_1$-$C_4$-alkyl.

10. The method according to claim 1, wherein
$R^4$ is H;
o is 0 or 1;
m is 0 or 1; and
n is 0 or 1.

11. The method according to claim 1, wherein
$Y^4$ is N;
$R^4$ is H;
o is 0 or 1;
m is 0 or 1; and
n is 0 or 1.

12. The method according to claim 1, wherein
$R^1$ is independently of its occurrence selected from the group consisting of halogen, CN, $C_1$-$C_4$-alkyl, fluorinated $C_1$-$C_4$-alkyl, and $C_1$-$C_4$-alkoxy;
$R^2$ is independently of its occurrence selected from the group consisting of halogen, CN, $C_1$-$C_6$-alkyl, halogenated $C_1$-$C_6$-alkyl, and $NR^aR^b$, wherein $R^a$ and $R^b$ are selected, independently of each other, from the group consisting of hydrogen and $C_1$-$C_4$-alkyl; or $NR^aR^b$ forms a saturated 5- or 6-membered heterocycle, selected from the group consisting of piperidin-1-yl, piperazin-1-yl, morpholin-4-yl, and pyrrolidin-1-yl;
$R^3$ is halogen;
m is 0 or 1;
n is 0 or 1;
o is 0 or 1;
$R^4$ is hydrogen; and
$Y^4$ is N.

13. The method according to claim 1, wherein the compound of formula (I) is selected from the group consisting of:
1-Pyrazin-2-yl-3-(6-trifluoromethyl-quinolin-4-yl)-urea;
1-Pyrazin-2-yl-3-(7-trifluoromethyl-quinolin-4-yl)-urea;
1-Pyrazin-2-yl-3-(8-trifluoromethyl-quinolin-4-yl)-urea;
1-(2-Methyl-quinolin-4-yl)-3-pyrazin-2-yl-urea;
1-Pyrazin-2-yl-3-quinolin-4-yl-urea;
1-Pyrazin-2-yl-3-(2-trifluoromethyl-quinolin-4-yl-urea;
1-(6-Bromo-quinolin-4-yl)-3-pyrazin-2-yl-urea;
1-Methyl-1-pyrazin-2-yl-3-(6-trifluoromethyl-quinolin-4-yl)-urea;
1-Pyrazin-2-yl-3-(1,2,3,4-tetrahydro-acridin-9-yl)-urea;
1-(Quinolin-4-yl)-3-(pyrazin-2-yl)urea;
1-(8-Fluoroquinolin-4-yl)-3-(pyrazin-2-yl)urea;
1-(7-Iodoquinolin-4-yl)-3-(pyrazin-2-yl)urea;
1-(7-Bromoquinolin-4-yl)-3-(pyrazin-2-yl)urea;
1-(Pyridin-2-yl)-3-(7-(trifluoromethyl)quinolin-4-yl)urea;
1-(8-Methylquinolin-4-yl)-3-(pyrazin-2-yl)urea;
1-(8-Chloroquinolin-4-yl)-3-(pyrazin-2-yl)urea;
1-(6-Morpholinopyridin-2-yl)-3-(8-(trifluoromethyl)quinolin-4-yl)urea;
1-(8-Iodoquinolin-4-yl)-3-(pyrazin-2-yl)urea;
1-(3-Bromoquinolin-4-yl)-3-(pyrazin-2-yl)urea;
1-(6,8-Difluoroquinolin-4-yl)-3-(pyrazin-2-yl)urea and;
1-(8-Bromoquinolin-4-yl)-3-(pyrazin-2-yl)urea;
or a stereoisomer, or physiologically tolerated acid addition salt thereof.

* * * * *